(12) United States Patent
Panse et al.

(10) Patent No.: US 11,069,146 B2
(45) Date of Patent: Jul. 20, 2021

(54) AUGMENTED REALITY FOR COLLABORATIVE INTERVENTIONS

(71) Applicant: KONINKLIJKE PHILIPS N.V., Eindhoven (NL)

(72) Inventors: Ashish Panse, Burlington, MA (US); Molly Lara Flexman, Melrose, MA (US); Atul Gupta, Andover, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/613,607

(22) PCT Filed: May 9, 2018

(86) PCT No.: PCT/EP2018/062013
§ 371 (c)(1),
(2) Date: Nov. 14, 2019

(87) PCT Pub. No.: WO2018/210656
PCT Pub. Date: Nov. 22, 2018

(65) Prior Publication Data
US 2020/0105068 A1 Apr. 2, 2020

Related U.S. Application Data

(60) Provisional application No. 62/506,916, filed on May 16, 2017.

(51) Int. Cl.
*G06T 19/00* (2011.01)
*G06F 3/01* (2006.01)
(Continued)

(52) U.S. Cl.
CPC .......... *G06T 19/006* (2013.01); *G02B 27/017* (2013.01); *G06F 3/011* (2013.01);
(Continued)

(58) Field of Classification Search
None
See application file for complete search history.

(56) References Cited

U.S. PATENT DOCUMENTS

| | | |
|---|---|---|
| 2013/0293468 A1 | 11/2013 | Perez et al. |
| 2014/0368537 A1 | 12/2014 | Salter et al. |
| 2018/0032130 A1* | 2/2018 | Meglan ................ G02B 27/017 |

FOREIGN PATENT DOCUMENTS

WO 2016133644 A1 8/2016

OTHER PUBLICATIONS

PCT/EP2018/062013 ISR & WO, Jul. 10, 2018, 16 Page Document.

* cited by examiner

*Primary Examiner* — Michelle Chin

(57) ABSTRACT

A controller for augmenting reality includes a memory that stores instructions, and a processor that executes the instructions. The controller receives, from at least one device that provides output via a display, an information feed comprising first visual information from the at least one device. When executed by the processor, the instructions cause the controller to execute a process comprising controlling generation of first visual information in a first shared portion of a three-dimensional (3D) space by a first augmented reality device as augmented reality, and controlling generation of the first visual information in the first shared portion of the 3D space by a second augmented reality device as augmented reality.

20 Claims, 19 Drawing Sheets

(51) Int. Cl.
  *G06F 3/033* (2013.01)
  *G02B 27/01* (2006.01)
  *A61B 17/00* (2006.01)
(52) U.S. Cl.
  CPC .............. *G06F 3/017* (2013.01); *G06F 3/033* (2013.01); *A61B 2017/00216* (2013.01)

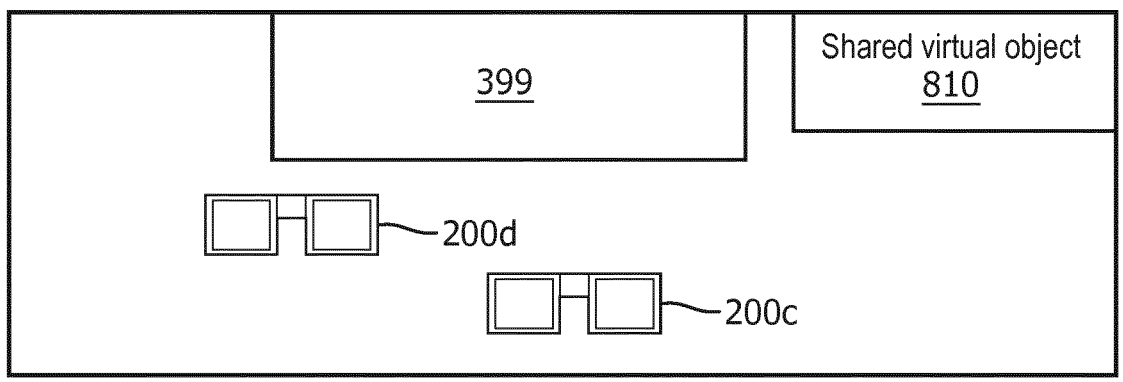
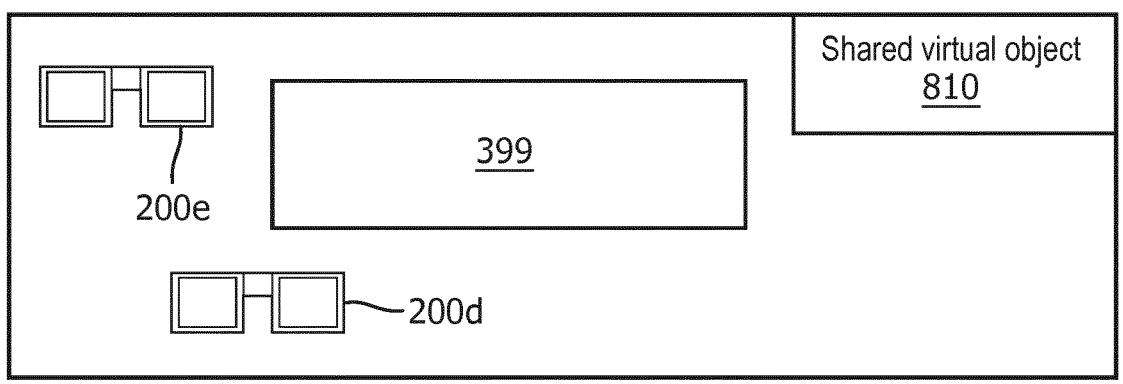
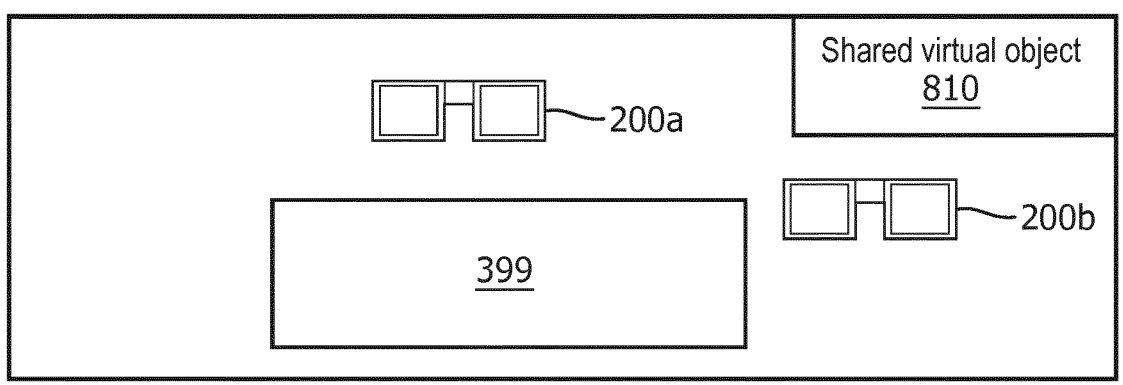
FIG. 8

| Shared portion 1 control 1401 | | | | | | |
|---|---|---|---|---|---|---|
| Segment 1 control: X1 | Segment 2 control: X2 | Segment 3 control: X3 | Segment 4 control: X4 | Segment 5 control: X5 | Segment 6 control: X6 | Segment 7 control: X7 |

| Shared portion 2 control 1402 | | | | | | |
|---|---|---|---|---|---|---|
| Segment 1 control: Y1 | Segment 2 control: Y2 | Segment 3 control: Y3 | Segment 4 control: Y4 | Segment 5 control: Y5 | Segment 6 control: Y6 | Segment 7 control: Y7 |

| Shared portion 3 control 1403 | | | | | | |
|---|---|---|---|---|---|---|
| Segment 1 control: Z1 | Segment 2 control: Z2 | Segment 3 control: Z3 | Segment 4 control: Z4 | Segment 5 control: Z5 | Segment 6 control: Z6 | Segment 7 control: Z7 |

First shared portion
810

Second shared portion
815

FIG. 15A 10 20 30 40 50 60 70 80 90 100 110 120 130 140 150 160 170 180

First shared portion
810

First unshared portion
851

FIG. 15B

AUGMENTED REALITY FOR COLLABORATIVE INTERVENTIONS

CROSS-REFERENCE TO PRIOR APPLICATIONS

This application is the U.S. National Phase application under 35 U.S.C. § 371 of International Application No. PCT/EP2018/062013, filed on May 9, 2018, which claims the benefit of U.S. Provisional Patent Application No. 62/506,916, filed on May 16, 2017. These applications are hereby incorporated by reference herein.

BACKGROUND

Medical procedures such as interventional procedures may require multiple staff to be present in an enclosed space such as an operating room. Each of the multiple staff may have a different expertise. To work effectively, each of the multiple staff must be able to share information with the others. Information to be shared may include, for example, pre-operative imaging and patient background, intraoperative imaging, live views, and patient vitals. The positioning of multiple staff in an enclosed space makes it difficult to share screens and jointly view and discuss available information.

Augmented reality generally refers to when a live image stream is supplemented with additional computer-generated information. The live image stream can be via the eye, cameras or communications devices such as smart phones and tables. The live image stream is augmented via display to the user via glasses, contact lenses, projections or on the communications devices. Current augmented reality systems can sense and respond to a variety of user actions including gesture recognition, head tracking, eye tracking, and voice recognition.

SUMMARY

According to an aspect of the present disclosure, a controller for augmenting reality includes a memory that stores instructions and a processor that executes the instructions. The controller receives, from at least one device that provides output via a display, an information feed including first visual information from the at least one device. When executed by the processor, the instructions cause the controller to execute a process that includes controlling generation of first visual information in a first shared portion of a three-dimensional (3D) space by a first augmented reality device as augmented reality, and controlling generation of the first visual information in the first shared portion of the 3D space by a second augmented reality device as augmented reality.

According to another aspect of the present disclosure, a method of operating a controller for augmenting reality in a 3D space includes storing instructions in a memory of the controller. The method includes receiving, at the controller and from a first device that provides output via a display, a first information feed including first visual information. The instructions are executed by a processor of the controller to perform a process. The process includes controlling generation of the first visual information in a first shared portion of the 3D space by a first augmented reality device as augmented reality. The process also includes controlling generation of the first visual information in the first shared portion of the 3D space by a second augmented reality device as augmented reality.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIG. 8 illustrates a 3D space with a shared virtual object fixed at a location within the fields of vision for multiple subjects wearing head-mountable devices, in accordance with an aspect of the present disclosure;

FIG. 14 illustrates timelines for augmented reality for collaborative interventions, in accordance with a representative embodiment;

FIGS. 15A-15C illustrate fields of view for three separate augmented reality devices for augmented reality for collaborative interventions, in accordance with a representative embodiment.

DETAILED DESCRIPTION

Figure 1:
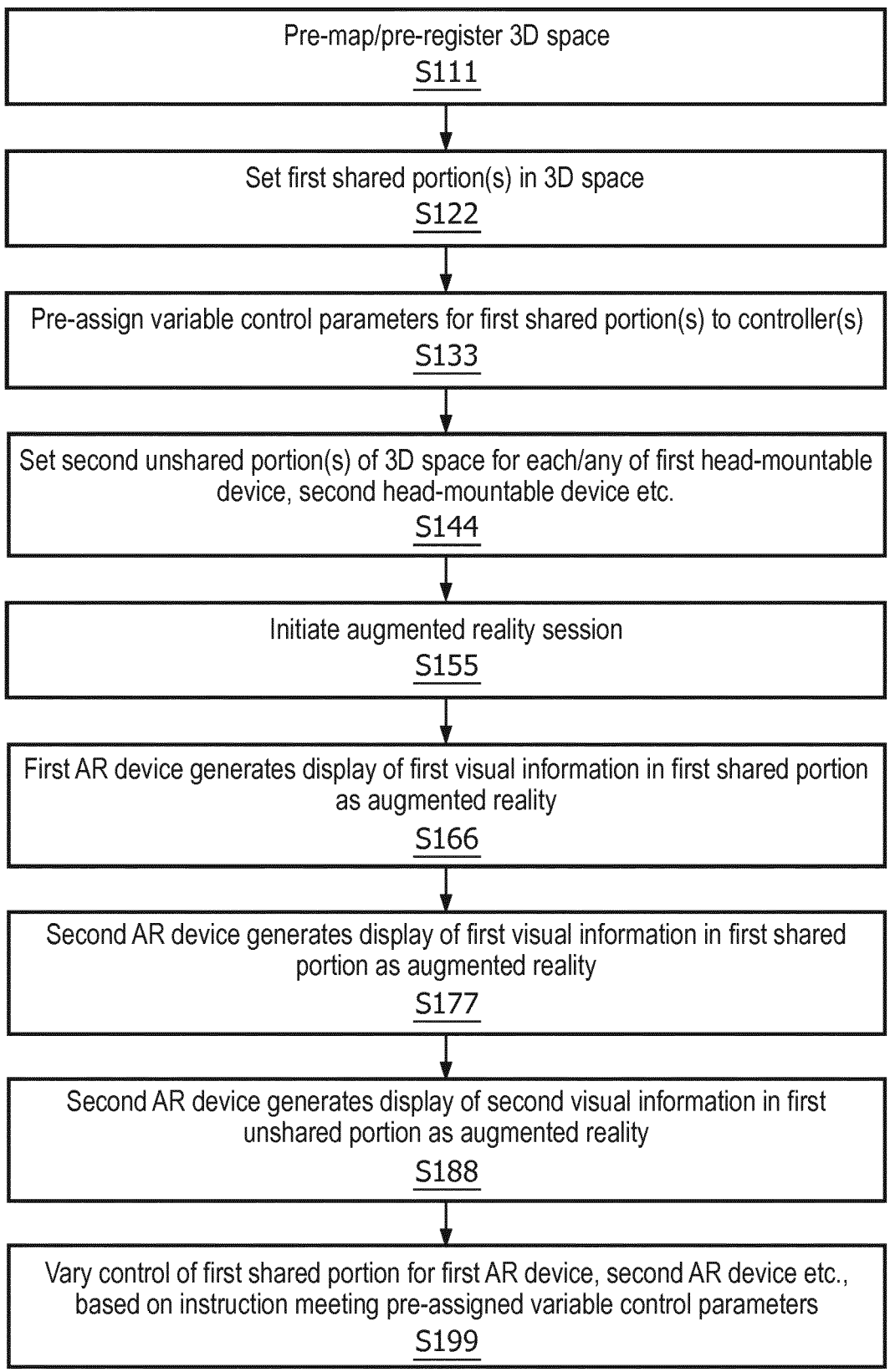
FIG. 1 illustrates a process for augmented reality for collaborative interventions, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing specific embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprise", and/or "comprising," and/or similar terms when used in this specification, specify the presence of stated features, elements, and/or components, but do not preclude the presence or addition of one or more other features, elements, components, and/or groups thereof. As used herein, the term "and/or" includes all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted to not obscure the description of the example embodiments. Such methods and apparatuses are within the scope of the present disclosure.

FIG. 1 illustrates a process for augmented reality for collaborative interventions, in accordance with a representative embodiment. The process shown in FIG. 1 may be representative of an overall process leading to varied control of a shared portion of a 3D space in augmented reality for collaborative interventions. The shared portion as described herein is a portion of the 3D space in which a virtual object is placed. The virtual object in the 3D space may be analogous to a display such as a white board, black board, television, computer monitor, hospital monitor (i.e., that outputs medical readings), or other forms of visual displays such as a 3D model of patient anatomy.

An example of a shared portion is as a data layer created by the creator of the shared portion. The creator may, for example, define a size and shape of a 2D or 3D shared portion, and locate the shared portion in a 3D space. Data defining the shared portion may define boundaries such as corners using coordinates derived from the mapping described below. Additionally, the shared portion may be a data layer defining the 2D or 3D space as visual data within the boundaries. As described in examples illustrated in FIGS. 16A-16C, the data layer may be controlled by a single controller at a time, and requests from others to add data to the data layer may be coordinated and controlled by the single controller. The data layer may then be superimposed on content from sources used to populate the shared portion.

At S111, the 3D space is pre-mapped and/or pre-registered. The 3D space may be mapped before a session in which augmented reality is provided, so the mapping at S111 is pre-mapping in a sense. The mapping may be performed by visually capturing all physical parameters of the 3D space and any physical items (e.g., furniture, equipment) in the 3D space. The 3D space may also be registered before the session in which augmented reality is provided, so the registering at S111 is also pre-registering in a sense. The registering may be performed by labelling each physical parameter of the 3D space and each physical item in the 3D space.

A computer program used to map and register the 3D space may be linked to a library of characteristics of physical parameters and physical items. A library of characteristics can be used to facilitate registering by linking any physical parameter or physical item identified in the mapping with a predetermined description. The mapping and registering are performed so that all areas in the 3D space in which virtual objects can be placed can be identified.

The mapping and registering can also be performed at the time of the AR session. For example, although the mapping at S111 is described above as pre-mapping, a 3D space can also be dynamically mapped after an augmented reality session begins, such as by using the sensors of augmented reality devices to collect parameters of a 3D space and then using image recognition to register the physical parameters and physical items in the 3D space.

At S122, a first shared portion of the 3D space is set. The first shared portion of the 3D space may be a volume of the 3D space reserved for placement of a virtual object or virtual objects. Alternatively, the virtual object or virtual objects may be placed in the first shared portion immediately once the first shared portion is set at S122. As an example, a virtual display may be assigned to a first shared portion set at S122, and a data source to provide data for the virtual display may then be assigned to the virtual display. The first shared portion of the 3D space may be outlined with a border or may be shaded a specific color to indicate it is shared. When the user moves their head to look at the region, there may be additional information that is shown to indicate who is sharing the first shared portion of the 3D space.

At S133, variable control parameters for the first shared portion are pre-assigned to a first head-mountable device, a second head-mountable device, and so on. That is, since the first shared portion is shared, control of the first shared portion must be established to be sure that multiple users do not alter the first shared portion at the same time or in ways not intended when the first shared portion is created.

As an example, a first subject may be made a "master" user in sole control of the first shared portion at S133, but the first subject may be able to pass the sole control on to another user before or during an augmented reality session. As another example, a first subject may be made a "master" user in sole control of the first shared portion for a first segment of the augmented reality session at S133, but a second subject may be made the "master" user in sole control of the first shared portion for a second segment of the augmented reality session at S133. In other words, in the latter example different subjects can be pre-assigned control of the first shared portion for different segments of a planned augmented reality session at S133.

At S144, a second unshared portion of the 3D space is set. An unshared portion of the 3D space is a portion of the 3D space that will only appear in the view of the subject wearing the head-wearable display configured to generate the unshared portion. The second unshared portion of the 3D space may be a volume of the 3D space reserved for placement of a virtual object or virtual objects. Alternatively, the virtual object or virtual objects may be placed in the second unshared portion immediately once the second unshared portion is set at S144. The first unshared portion of the 3D space may be outlined with a border or may be shaded a specific color to indicate it is shared.

As should be clear, unshared portions may be pre-set for any of the head-mountable devices involved in a planned augmented reality session. Accordingly, different subjects may be provided with different virtual reality objects in their views during the augmented reality session.

Any shared portion or unshared portion of the 3D space may be occupied by a virtual object analogous to a display such as a white board, black board, television, computer monitor, hospital monitor (i.e., that outputs medical readings), 3D models, or other forms of visual displays. Therefore, while a shared portion may be used to present the same information in the view of multiple or even all subjects wearing head-mountable devices, unshared portions may be used to present segregated information in the view of a single subject wearing a head-mountable device without exposing the information to other subjects engaged in the augmented reality session.

At S155, an augmented reality session is initiated. An augmented reality session may be considered to start when a first subject wearing a head-mountable device enters a 3D space. Moreover, multiple augmented reality sessions may take place simultaneously, wherein each of multiple different subjects wearing head-mountable devices individually enters the 3D space. The head-mountable devices may be pre-programmed or preauthorized to access the shared portion of the 3D space which is occupied by a virtual reality object. For example, augmented reality sessions may correspond to a medical intervention occurring in a pre-mapped operating room serving as the 3D space, and each subject authorized to access the virtual reality object may access information displayed via the virtual reality object during the medical intervention. Additionally, while mapping and registering of a 3D space are described herein as being done preliminary to a augmented reality session, the mapping and registering can also be performed dynamically at the beginning or even throughout an augmented reality session. For example, mapping and registering can be performed dynamically using sensors on augmented reality devices to sense parameters of the 3D space and physical items in the 3D space, and using image recognition programs to recognize and label the parameters and physical items.

At S166, a first head-mountable device generates a display of first visual information in the first shared portion as augmented reality. At S177, a second head-mountable device separately generates a display of the first visual information in the first shared portion as augmented reality.

To be clear, the first visual information and the first shared portion are not restricted to head-mountable devices. Rather, head-mountable devices are readily explained in the context of a 3D space such as an operating room and are used as examples for convenience herein. The virtual reality object occupying the first shared portion may be displayed to any authorized subject with a view of the 3D space that includes the shared portion. For example, even a remote user watching the 3D space via a camera may have access to the first shared portion when the remote user is so authorized. In addition to head-mountable devices, users with access to a first shared portion may use projected images, transparent heads-up displays, and other forms of augmented reality devices.

At S188, the second head-mountable device generates a display of second visual information in a first unshared portion as augmented reality. S188 illustrates that a shared portion of a 3D space is differentiated from an unshared portion, in that an unshared portion may be to a single augmented reality device. In other words, an unshared portion may not be visible to any other augmented reality device. On the other hand, a shared portion of a 3D space may be visible to multiple augmented reality devices, but is not necessarily visible to all augmented reality devices. Therefore, different shared portions of a 3D space occupied by virtual objects may be visible to different groups of users.

At S199, control of a first shared portion is varied, based on an instruction meeting the pre-assigned variable control parameters from S133. For example, control may be passed from a central computer that initially controls the first shared portion to a user wearing a head-mountable device when the first head-mountable device enters the 3D space or when the authorized user requests controls of the first shared portion. In this way, content from data feeds may be changed on a display in the virtual object occupying the first shared portion. A data feed may be added or subtracted according to whoever controls the first shared portion. Additional subjects may be given access to the first shared portion, and access may be removed from existing subjects with access based on the control of the authorized subject.

Figure 2A:
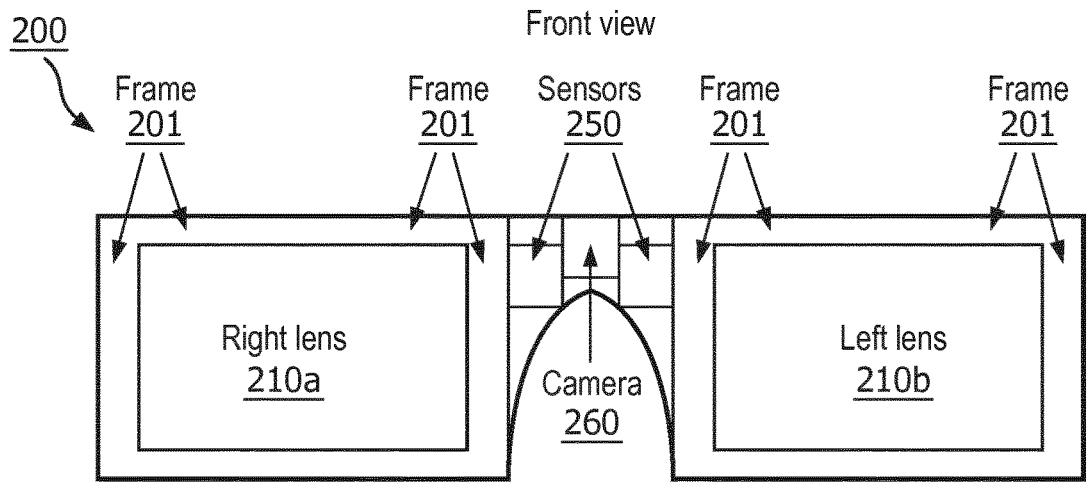
FIG. 2A illustrates a front view of a head-mountable device for augmented reality for collaborative interventions, in accordance with an aspect of the present disclosure.

FIG. 2A illustrates a front view of a head-mountable device for augmented reality for collaborative interventions, in accordance with an aspect of the present disclosure. In FIG. 2a, head-mountable device 200 includes a frame 201 in which a right lens 210a and a left lens 210b are separately enclosed. Sensors 250, camera 260 are representative of electronic components integrated in and/or on the frame 201.

As explained herein, the left lens 210b and the right lens 210a may each be provided in front of, or behind, a transparent optical display. Transparent optical displays may be controlled by image processors to generate virtual objects that are superimposed in the field of view of the subject wearing the head-mountable device 200. Alternatively, the left lens 210b and the right lens 210a may each be provided in front of mirrors that reflect light from a projector into the eyes of the subject wearing the head-mountable device 200. The effect of mirrors is the same as the effect of using transparent optical displays in that virtual objects are superimposed in the field of view of the subject wearing the head-mountable device 200.

The camera 260 faces forward to provide a forward view from the viewpoint of the subject wearing the head-mountable device 200. The camera 260 may be representative of multiple cameras, including cameras of different types (RBG, grayscale, depth sensing cameras, IR cameras, spectral cameras). The sensors 250 sense aspects of the environment around the head-mountable device 200.

The sensors 250 may include, for example, accelerometers, gyroscopes, resistive sensors, current sensors, piezoelectric sensors, voltage sensors, capacitive sensors, global positioning satellite receivers, compasses, altimeters, cameras, rangefinders, microphones, thermometers, chemical sensors, moisture sensors, and so on. The sensors 250 sense movement of the subject wearing the head-mountable device 200, such as when and by how much the subject tilts or swivels their head. The sensors 250 also sense environmental conditions of the environment around the head-mountable device 200, such as temperature and humidity, lighting conditions. As explained below relative to FIG. 2C, cameras 270a, 270b may also be provided as sensors to track eye movements of the operator.

Figure 2B:
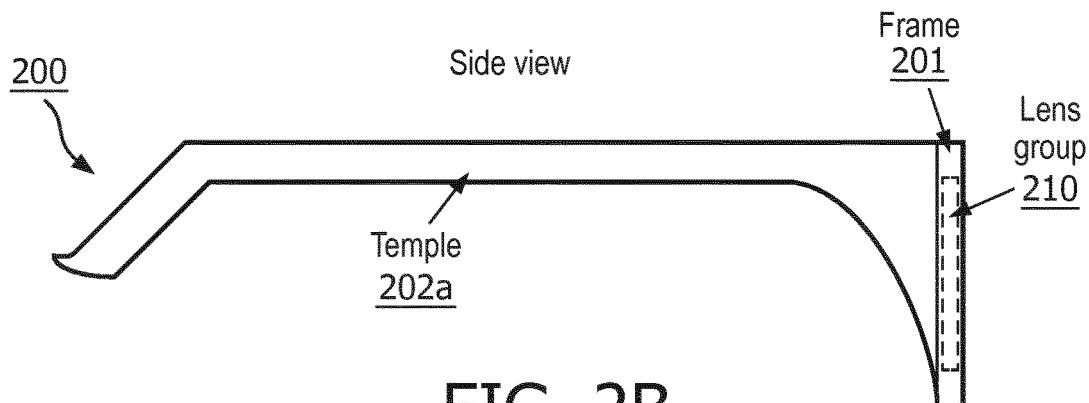
FIG. 2B illustrates a side view of a head-mountable device for augmented reality for collaborative interventions, in accordance with an aspect of the present disclosure.

FIG. 2B illustrates a side view of a head-mountable device for augmented reality for collaborative interventions, in accordance with an aspect of the present disclosure. In FIG. 2B, a right temple 202a is shown extending from a lens group 210 enclosed in the frame 201. The lens group 210 includes the right lens 210a and left lens 210b as shown in FIG. 2A.

The right temple 202a is for the right side of the head of the subject wearing the head-mountable device 200. A left temple 202b is provided for the left side of the head of the subject wearing the head-mountable device 200, as is explained below with respect to FIG. 2C. The right temple 202a is used to hold the head-mountable device 200 over an ear of the subject wearing the head-mountable device 200. As shown in FIG. 2A, the middle portion of the front of the head-mountable device 200 can also be balanced on a nose of the subject wearing the head-mountable device 200.

Figure 2C:
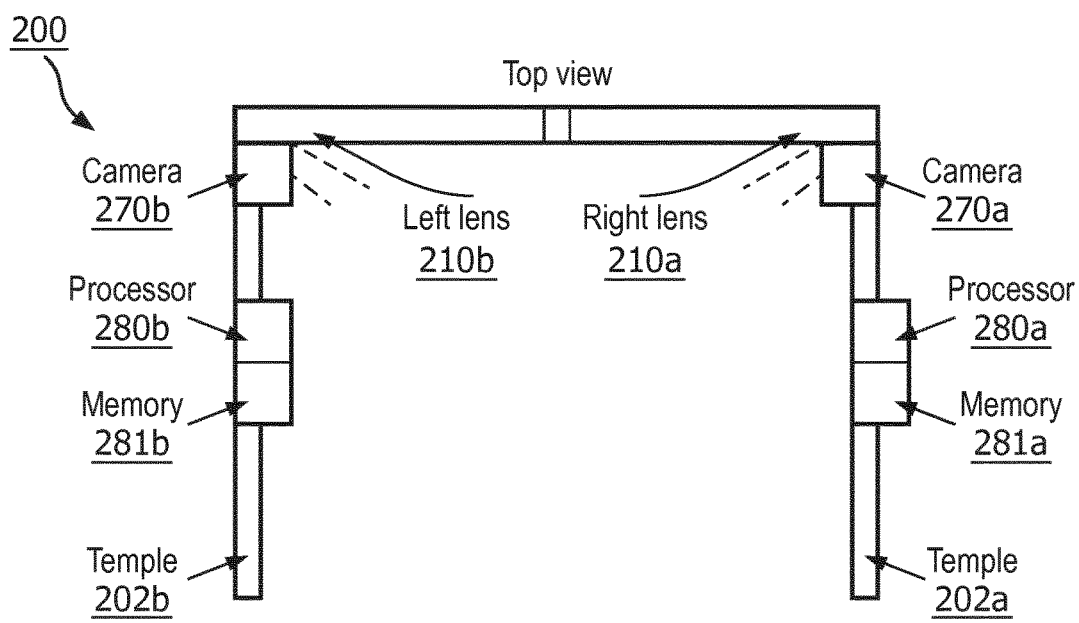
FIG. 2C illustrates a top view of a head-mountable device for augmented reality for collaborative interventions, in accordance with an aspect of the present disclosure.

FIG. 2C illustrates a top view of a head-mountable device for augmented reality for collaborative interventions, in accordance with an aspect of the present disclosure. In FIG. 2C, a variety of electronic elements are shown disposed along the right temple 202a and left temple 202b. The elements include a camera 270a along the right temple 202a, and a camera 270b along the left temple 202b. The left temple 202b also includes a processor 280b and a memory 281b, and the right temple 202a also includes a processor 280a and a memory 281a. The processors 280a, 280b and memories 281a, 281b are representative of elements of a general computer system which may be entirely or partially included in the head-mountable device 200.

The cameras 270a, 270b face rearward, and are used to capture eye movements of the subject wearing the head-mountable device 200. Though the cameras 270a, 270b are shown separate from the sensors 250 from FIG. 2A, the cameras 270a, 270b are consistent with a type of the sensors 250 in that they sense movement of the eyes of the subject wearing the head-mountable device 200.

The memories 281a, 281b store instructions and data for the head-mountable device 200, and the processors 280a, 280b execute the instructions for the head-mountable device 200. The instructions stored in memories 281a, 281b and executed by processors 280, 280b may include instructions for generating specific virtual objects to be superimposed in the field of view of the subject wearing the head-mountable device 200.

Figure 3A:
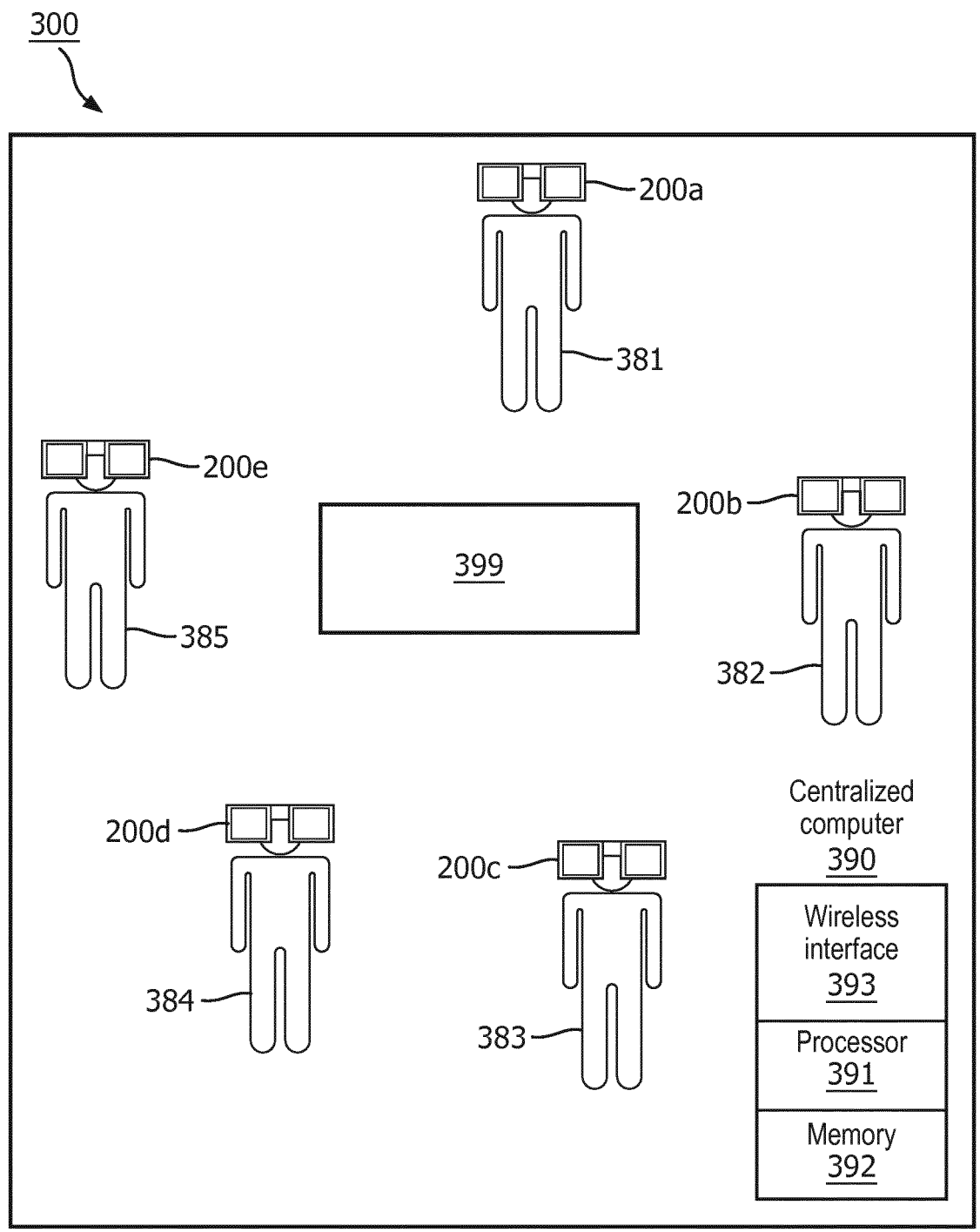
FIG. 3A illustrates a 3D space with subjects wearing head-mountable devices for augmented reality for collaborative interventions, in accordance with an aspect of the present disclosure.

FIG. 3A illustrates a space with subjects wearing head-mountable devices for augmented reality for collaborative interventions, in accordance with an aspect of the present disclosure. In FIG. 3A, five subjects 381-385 are shown disposed around a table 399 in the 3D space 300. Also in FIG. 3A, a centralized computer 390 is shown with a wireless interface 393, a processor 391 and a memory 392.

The centralized computer 390 may be used to initially control a shared portion of the 3D space 300. Control of the shared portion of the 3D space may be passed to one of the five subjects 381-385 when a head-mountable device 200a-200e is activated. The passing of control may be according to predetermined instructions stored in the memory 392 and executed by the processor 391. The predetermined instructions for control of a shared space may allow one of the five subjects 381-385 or another subject in the 3D space 300 or outside of the 3D space 300 to change control of the shared portion of the 3D space.

The five subjects 381-385 include first subject 381, second subject 382, third subject 383, fourth subject 384 and fifth subject. First subject 381 is wearing a first head-mountable device 200a, the second subject 382 is wearing a second head-mountable device 200b, the third subject 383 is wearing a third head-mountable device 200c, the fourth subject 384 is wearing a fourth head-mountable device 200d, and the fifth subject 385 is wearing a fifth head-mountable device 200e. Each of the first head-mountable device 200a, second head-mountable device 200b, third head-mountable device 200c, fourth head-mountable device 200d and fifth head-mountable device 200e described herein may include any of the features specifically described with respect to the head-mountable device 200 shown in FIGS. 2A-2C. Additionally, each of the head-mountable devices 200a-200e may be wirelessly connected to each of the other head-mountable devices 200a-200e, as well as to the centralized computer 390. Each of the head-mountable devices 200a-200e may also be tethered to the centralized computer 390.

The 3D space 300 may be a room, such as an operating room in a hospital, and the five subjects 381-385 may be personnel such as medical personnel involved in a medical intervention for a patient disposed on the table 399. The teachings of the present disclosure are not limited to operating rooms or medical personnel, but for convenience this setting for the teachings herein may be repeatedly referenced.

In the operating room example, five subjects 381-385 may each have different responsibilities and rely on different information sources that provide different kinds of information. The five subjects 381-385 may also have responsibilities that rely on the same information source or information sources. As seen in FIG. 3A, it would be difficult to provide a common information source to the five subjects 381-385 via a single monitor since they are disposed around the table 399, and this would be particularly difficult for any personnel that are required to visually monitor a patient on the table 399 directly.

The 3D space 300 is an enclosure such as an operating room, and may be pre-mapped so that every physical object in the 3D space 300 is mapped in preparation for the augmented reality for collaborative interventions described herein. The pre-mapping for the 3D space may be used therefore to provide each of the five subjects 381-385 with augmented reality. That is, the pre-mapping provides physical constraints that cannot be altered, whereas virtual objects can be provided in the 3D space in locations that do not conflict with the pre-mapped physical constraints.

In FIG. 3A, the head-mountable devices 200a-200e are used to provide augmented reality for collaborative interventions. Each head-mountable device 200 is configured to provide a transparent interface for the subject wearing the head-mountable device 200, so that when reality is not being augmented the subject is given an unaltered view of the physical world as seen through the head-mountable device 200. When reality is being augmented as described herein, the head-mountable device 200 is used to augment the view of the physical world with virtual objects superimposed in the view of the physical world.

As described herein, each of the subjects 281-285 may be provided a dedicated unshared portion of the 3D space by the head-mountable devices 200a-200e. In other words, each of the head-mountable devices 200a-200e may uniquely provide a corresponding subject with a dedicated portion of the 3D space that will not appear in the view of the 3D space for another of the head-mountable devices 200a-200e. These dedicated portions shown in the view of only one of the five subjects 381-385 are described herein as unshared portions.

Also, as described herein, multiple of the five subjects 381-385 may be provided a common shared portion of the 3D space by the head-mountable devices 200a-200e. In other words, multiple of the head-mountable devices 200a-200e may provide corresponding subjects with the same portion of the 3D space. These portions shown in the view of multiple of the five subjects 381-385 are described herein as shared portions.

Figure 3B:
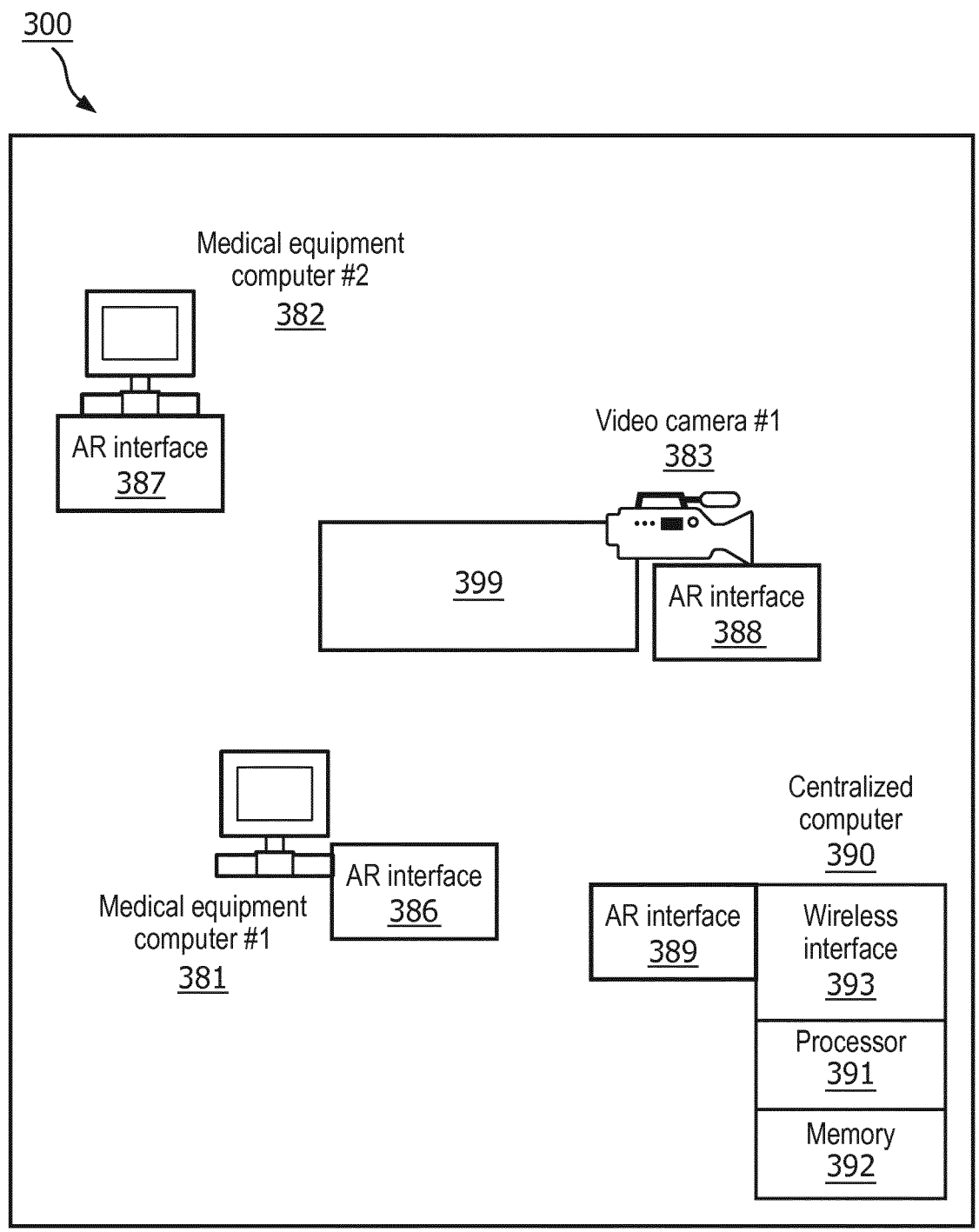
FIG. 3B illustrates another view of the 3D space in FIG. 3A with medical equipment provided with augmented reality interfaces for augmented reality for collaborative interventions, in accordance with an aspect of the present disclosure.

FIG. 3B illustrates another view of the 3D space in FIG. 3A with medical equipment provided with augmented reality interfaces for augmented reality for collaborative interventions, in accordance with an aspect of the present disclosure. In FIG. 3B, multiple different electronic devices are used to monitor and/or display medical information for a patient on the table 399.

A video camera #1 383 is used to provide a video feed of the patient during a medical intervention. An augmented reality interface 388 is used to selectively provide the video feed from video camera #1 383 to personnel via augmented reality.

A medical equipment computer #1 381 is used to obtain and display medical information from sensors on or around the patient. An augmented reality interface 386 is used to selectively provide the medical information to personnel via augmented reality.

A medical equipment computer #2 382 is also used to obtain and display medical information from sensors on or around the patient. An augmented reality interface 387 is used to selectively provide the medical information to personnel via augmented reality.

The centralized computer 390 is shown in FIG. 3B, and may be used to control, at least initially, the augmented reality provided via a shared portion of the 3D space 300. As noted, the centralized computer 390 includes a processor 391, memory 392, and a wireless interface 393. The centralized computer 390 may control the shared portion(s) of the 3D space by restricting an ability to view the shared portion(s), restricting an ability to alter the feeds provided via the shared portion(s), and restrict the ability to interact within the shared portion(s). As noted elsewhere herein, the control provided by the centralized computer 390 may vary, such as when an authorized user switches control of the shared portion(s) from the centralized computer 390 to another authorized user using, for example, a head-mountable device 200.

As an example of FIG. 3B, the 3D space 300 may be a sample room layout for an operating room used for a complex minimally-invasive structural heart procedure. In this procedure, multiple people in the room need to work together effectively to treat the patient. These people may include, for example:

An anesthesiologist to administer anesthesia and monitor the patient.
An echocardiographer to position a TEE probe and control ultrasound image acquisition.
An interventionalist #1 to navigates catheters, guidewires, and other devices to deliver therapy to the patient.
Interventionalists #2-3 to assist interventionalist #1.
A Nurse to bring appropriate tools and devices to the Interventionalists.
An X-ray technician to assist with operating an interventional x-ray system.

Examples of the information required for the people in the above example can include:

An intra-operative x-ray (live image, roadmaps, reference images)
An intra-operative ultrasound (TEE, ICE, IVUS, etc.)
Pre-operative imaging (Ultrasound, CT, MRI)
Patient history
Patient vitals, hemodynamics
Dose information (for staff—DoseAware, or patient)
Live views of what different people are seeing.
Overlays on live imaging
Targets/markers In the example above, augmented reality interface 386, augmented reality interface 387, and augmented reality interface 388 may be used to provide the information to a shared portion of the 3D space that is visible using augmented reality. This avoids requiring multiple monitors positioned throughout the room, and helps provide each authorized person using the shared augmented reality with a common perspective to observe the patient, the monitors, and each other.

Additionally, in the example above, a person may have access using augmented reality even when the person leaves the 3D space 300. For example, a nurse wearing a head-mountable device may leave the room to retrieve equipment and maintain communication and access to the first shared portion of the 3D space visible via augmented reality. The same access to the first shared portion can be provided for staff members sitting in an external control room, or senior staff members supervising junior staff members who may be called away to consult in a neighboring room.

Figure 4:
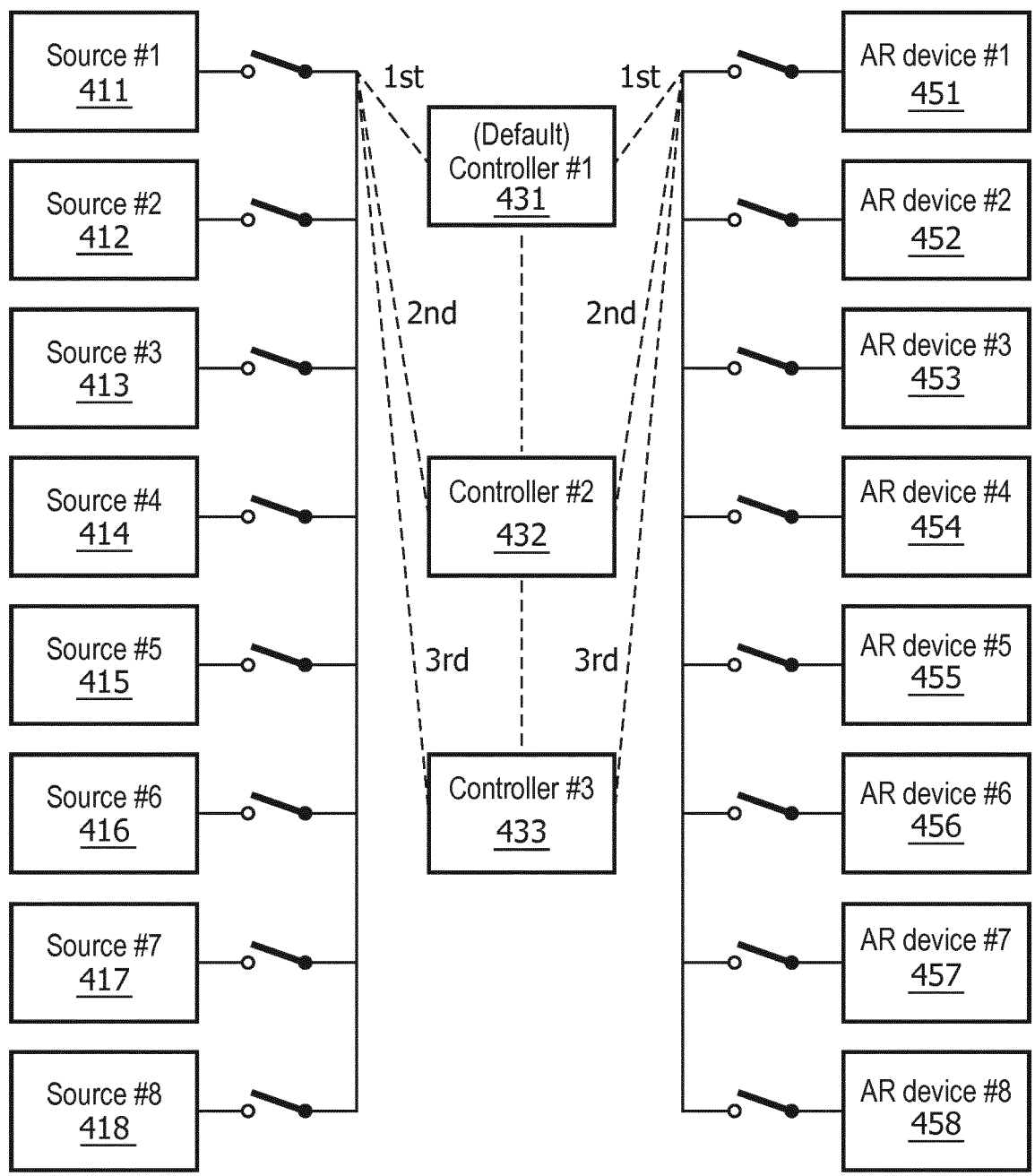
FIG. 4 illustrates a logical arrangement demonstrative of control of a shared portion of a 3D space for augmented reality for collaborative interventions, in accordance with an aspect of the present disclosure.

FIG. 4 illustrates a logical arrangement demonstrative of control of a shared portion of a 3D space for augmented reality for collaborative interventions, in accordance with an aspect of the present disclosure. In FIG. 4, a column of sources 411-418 on the left are each switchable in and out of a stream. A column of augmented reality devices 451-458 on the right are also each switchable in and out of a stream. Data, information and content from the sources 411-418 can be selectively provided to the augmented reality devices 451-458 via the stream.

The middle column in FIG. 4 shows a column of controllers 431, 431, 433. Controller 431 may be a default controller for an augmented reality session, so that when the augmented reality session starts the controller 431 initially controls which sources 411-418 are used to provide data, information and content to the shared portion of the 3D space. The controller 431 may also initially control which augmented reality devices 451-458 will receive the data, information and content in the shared portion of the 3D space. The controller 431 may also switch the control of the shared portion of the 3D space to controller 432 or to controller 433, such as based upon a dynamic instruction from a user, based on passage of a predetermined time, or based on passage of a predetermined segment of the augmented reality session.

That is, as described above, at least three types of control are exercised by a controller 431, 432 or 433 for a shared portion of a 3D space. The controller 431, 432 or 433 exercises control by, for example:
- selectively adding or removing any source 411-418 to or from a stream provided to a shared portion of the 3D space.
- selectively adding or removing any augmented reality device 451-458 to/from access to the stream provided to the shared portion of the 3D space.
- selectively passing control of the stream and the shared portion of the 3D space to another controller.

Communications address of the sources 411-418 and augmented reality devices 451-458 can be used to implement the control. For example, each augmented reality device 451-458 may correspond to a unique communications address, and the communications address can be added to or removed from a list of authorized destinations for a stream. Similarly, each of the sources 411-418 may correspond to a unique communications address, and the communications address can be added to or removed from a list of authorized sources for a stream.

Though switches are shown between the sources 411-418 and the controllers 431-433, and between the controllers 431-433 and the augmented reality devices 451-458, physical switches are not particularly required to individually switch sources 411-418 and augmented reality devices 451-458 in and out of the stream. Rather, control can be logically exercised and implemented using, for example, a processor 391 and memory 392 in FIG. 3A, or any corresponding processor/memory pair in any other augmented reality computer/computing device described herein.

Figure 5A:
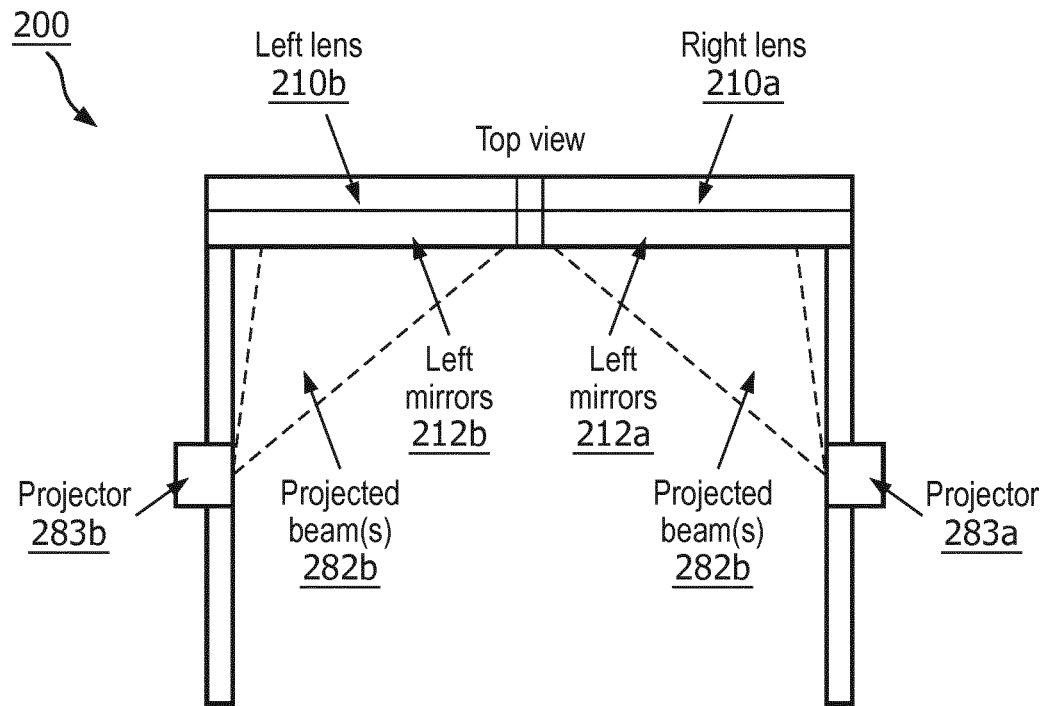
FIG. 5A illustrates a top view of another head-mountable device for augmented reality for collaborative interventions, in accordance with an aspect of the present disclosure.

FIG. 5A illustrates a top view of another head-mountable device for augmented reality for collaborative interventions, in accordance with an aspect of the present disclosure. In FIG. 4, a combination of projector 283b and left mirrors 212b may form all or part of a display system. Similarly, a combination of projector 283a and right mirrors 212a may form all or part of a display system. The display systems work by the projectors 283a, 283b projecting light that is reflected by mirrors 212a, 212b into the eyes of the subject wearing the head-mountable device 200. The projectors 283a, 283b may operate together with the processors 280a, 280b from FIG. 2 to generate virtual objects superimposed in the view of the subject wearing the head-mountable device 200. The processors 280a, 280b may provide image data for each virtual object for the head-mountable device 200, and projectors 283a, 283b may project light for the left mirrors 212b and right mirrors 212a to reflect to display the images for each virtual object.

The mirrors 212a, 212b may be matrices of small mirrors arranged as a digital micromirror device DMD, for a digital light processing (DLP) projector. In any event, in FIG. 4, the left mirrors 212b and the right mirrors 212a are transparent, so that when no light is reflected by the left mirrors 212b and the right mirrors 212a, the subject wearing the head-mountable device 200 will have a view of the unaltered physical world. However, the projectors 283a, 283b may, in operation, operate with the left mirrors 212b and the right mirrors 212a to generate the virtual objects that are superimposed in the field of view of the subject wearing the head-mountable device 200.

Figure 5B:
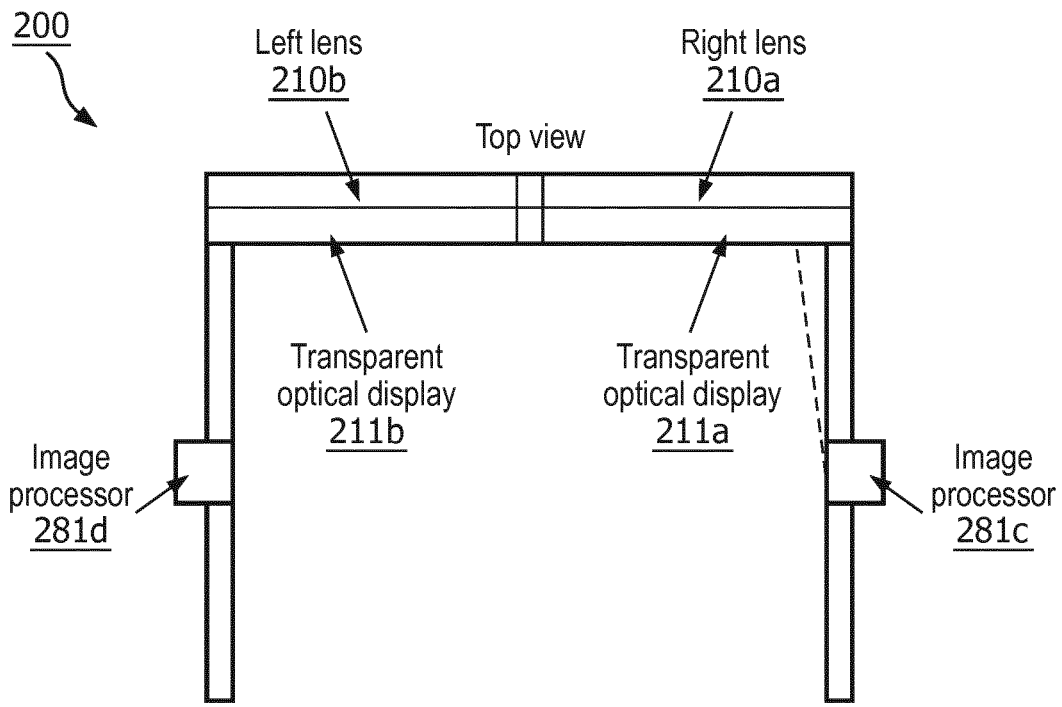
FIG. 5B illustrates a top view of another head-mountable device for augmented reality for collaborative interventions, in accordance with an aspect of the present disclosure.

FIG. 5B illustrates a top view of another head-mountable device for augmented reality for collaborative interventions, in accordance with an aspect of the present disclosure. In FIG. 5, a transparent optical display 211b is provided behind the left lens 210b, and a transparent optical display 211a is provided behind the right lens 210a. Image processor 281d controls elements of the transparent optical display 211b, and image processor 281c controls elements of the transparent optical display 211a.

In FIG. 5, the combination of image processor 281d and transparent optical display 211b may form all or part of a display system. The combination of image processor 281c and transparent optical display 211a may form all or part of a display system. The image processors 281c, 281d may operate together with the processors 280a, 280b from FIG. 2 to generate virtual objects superimposed in the view of the subject wearing the head-mountable device 200. That is, the processors 280a, 280b may provide image data for each virtual object for the head-mountable device 200, and image processors 281c, 281d may control the individual elements of the transparent optical displays 211a, 211b to display the images for each virtual object.

The transparent optical displays 211a, 211b may, for example, simultaneously allow subjects to view the physical world and artificially generated virtual objects. The transparent optical displays 211a, 211b may include, for example, transparent and polarized OLEDs, light-guide optical elements, and similar materials arranged in a matrix that can be individually and logically controlled, i.e., without a projected beam as in FIG. 4. Examples of the elements and materials that can be used for transparent optical displays 211a, 211b include an electroluminescent display elements, liquid crystal display (LCD) elements, and waveguides, reflective coatings.

FIGS. 5A and 5B show two examples of specific display systems that can be used to generate displays of virtual objects for augmented reality. It should be apparent that other types of display systems can be used to generate such displays of virtual objects consistent with the teachings of the present disclosure, and these two exemplary FIGs. are merely representative of mechanisms by which teachings herein can be implemented. Moreover, virtual objects may be superimposed on one another in the field of view of a user. As described herein, a shared portion may be defined as a data layer with specified borders defined by coordinates, and the data layer may be superimposed on content such as video content used to populate the shared portion. In other words, data including visual data may be dynamically superimposed as one virtual object on another virtual object, and both may then be superimposed in the field of view of a user as augmented reality.

Figure 6:
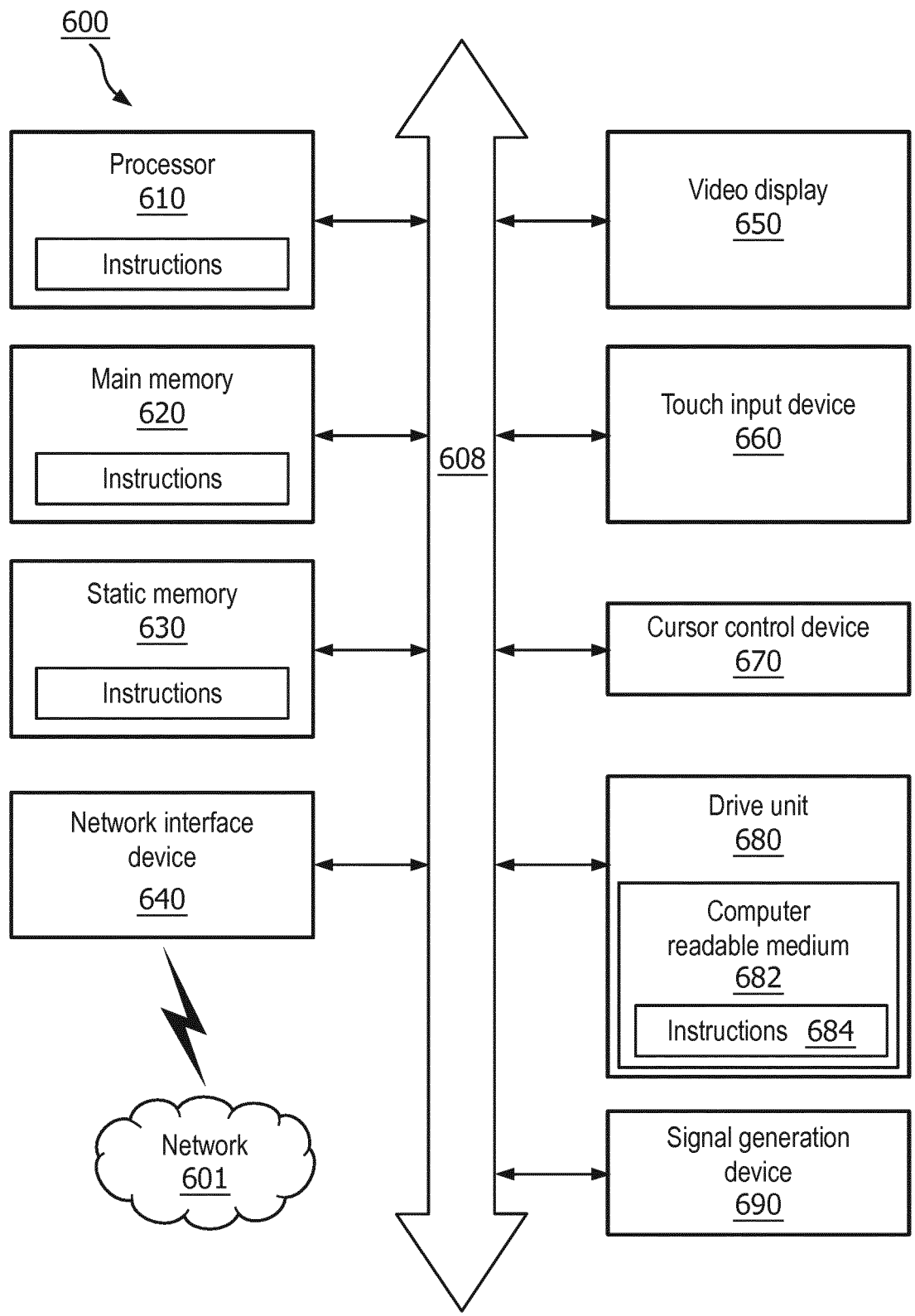
FIG. 6 illustrates an exemplary general computer system that includes a set of instructions for augmented reality for collaborative interventions, in accordance with an aspect of the present disclosure.

FIG. 6 is an illustrative embodiment of a general computer system 600, on which a method of augmented reality for collaborative interventions can be implemented. The computer system 600 can include a set of instructions that can be executed to cause the computer system 600 to perform any one or more of the methods or computer based functions disclosed herein. The computer system 600 may operate as a standalone device or may be connected, for example, using a network 603, to other computer systems or peripheral devices.

In a networked deployment, the computer system 600 may operate in the capacity of a server or as a client user computer in a server-client user network environment, or as a peer computer system in a peer-to-peer (or distributed) network environment. The computer system 600 can also be implemented as or incorporated into various devices, such as a head-mountable device, a stationary computer, a mobile computer, a personal computer (PC), a laptop computer, a tablet computer, a wireless smart phone, a personal digital assistant (PDA), a communications device, or any other machine capable of executing a set of instructions (sequential or otherwise) that specify actions to be taken by that machine. The computer system 600 can be incorporated as or in a device that in turn is in an integrated system that includes additional devices. In an embodiment, the computer system 600 can be implemented using electronic devices that provide voice, video or data communication. Further, while computer system 600 is individually illustrated, the term "system" shall also be taken to include any collection of systems or sub-systems that individually or jointly execute a set, or multiple sets, of instructions to perform one or more computer functions.

As illustrated in FIG. 6, the computer system 600 includes a processor 610. A processor for a computer system 600 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor for a computer system 600 is configured to execute software instructions to perform functions as described in the various embodiments herein. A processor for a computer system 600 may be a general-purpose processor or may be part of an application specific integrated circuit (ASIC). A processor for a computer system 600 may also be a microprocessor, a microcomputer, a processor chip, a controller, a microcontroller, a digital signal processor (DSP), a state machine, or a programmable logic device. A processor for a computer system 600 may also be a logical circuit, including a programmable gate array (PGA) such as a field programmable gate array (FPGA), or another type of circuit that includes discrete gate and/or transistor logic. A processor for a computer system 600 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 600 includes a main memory 620 and a static memory 630 that can communicate with each other via a bus 608. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 600 may further include a video display unit 650, such as a liquid crystal display (LCD), an organic light emitting diode (OLED), a flat panel display, a solid-state display, or a cathode ray tube (CRT). Additionally, the computer system 600 may include an input device 660, such as a keyboard/virtual keyboard or touch-sensitive input screen or speech and even voice input with speech and voice recognition, and a cursor control device 670, such as a mouse or touch-sensitive input screen or pad. The computer system 600 can also include a disk drive unit 680, a signal generation device 690, such as a speaker or remote control, and a network interface device 640. A computer system 600 may also include additional inputs (not shown) such as sensors that track poses (e.g., arm movement, eye movement, head movement) of one or more users in the environment around the computer system 600.

In an embodiment, as depicted in FIG. 6, the disk drive unit 680 may include a computer-readable medium 682 in which one or more sets of instructions 684, e.g. software, can be embedded. Sets of instructions 684 can be read from the computer-readable medium 682. Further, the instructions 684, when executed by a processor, can be used to perform one or more of the methods and processes as described herein. In an embodiment, the instructions 684 may reside completely, or at least partially, within the main memory 620, the static memory 630, and/or within the processor 610 during execution by the computer system 600.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 682 that includes instructions 684 or receives and executes instructions 684 responsive to a propagated signal; so that a device connected to a network 601 can communicate voice, video or data over the network 601. Further, the instructions 684 may be transmitted or received over the network 601 via the network interface device 640.

Figure 7:
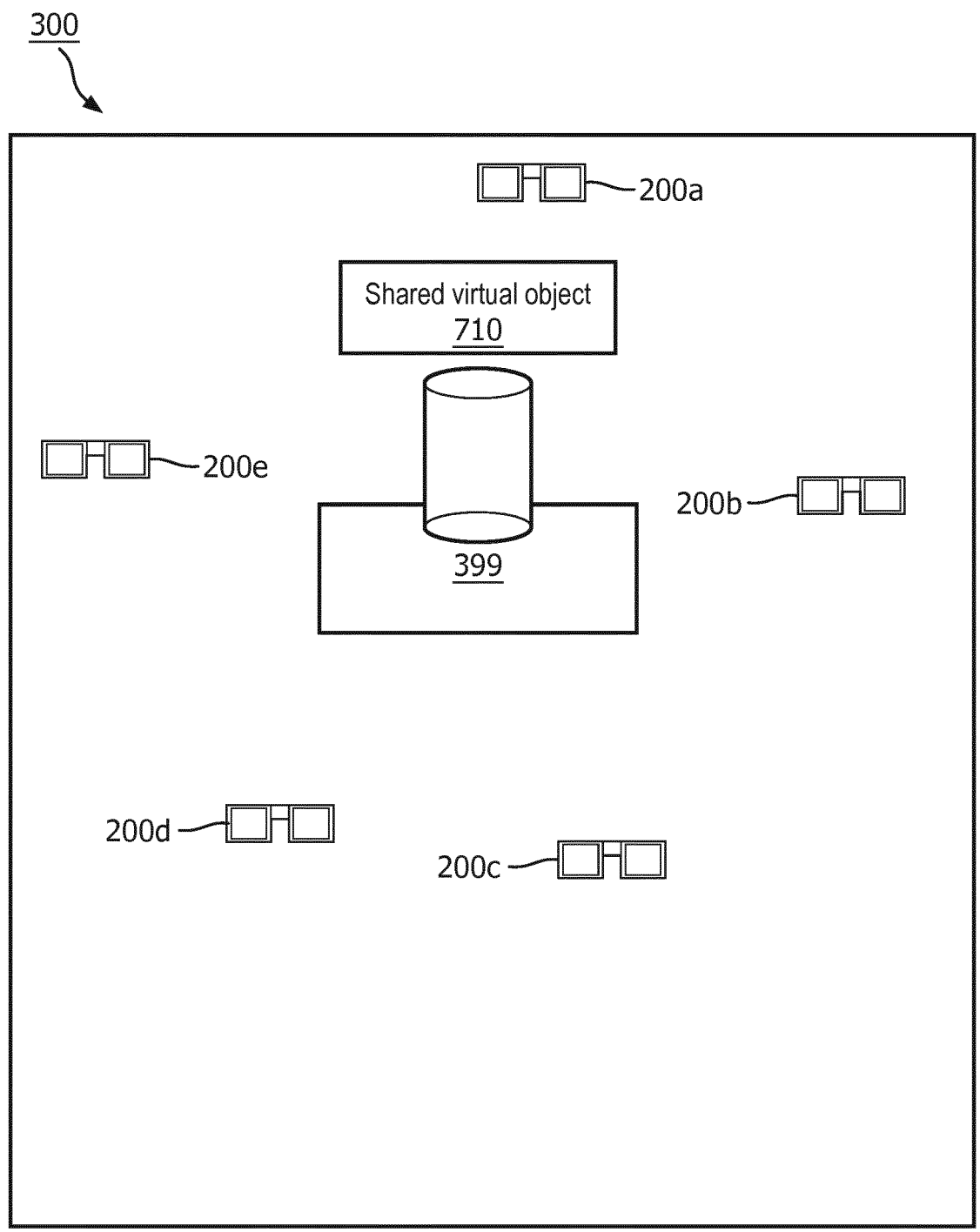
FIG. 7 illustrates a 3D space with a shared virtual object fixed at a location within the 3D for augmented reality for collaborative interventions, in accordance with an aspect of the present disclosure.

FIG. 7 illustrates an exemplary space with a shared virtual object fixed at a location within the 3D space for augmented reality for collaborative interventions, in accordance with an aspect of the present disclosure. In FIG. 7, a shared virtual object 710 is shown in the 3D space 300. The shared virtual object in FIG. 7 is a 3D object, and may represent a reserved space that will be shared by the subjects wearing the first head-mountable device 200a, second head-mountable device 200b, third head-mountable device 200c, fourth head-mountable device 200d and fifth head-mountable device 200e. In FIG. 7, the shared virtual object 710 is in a fixed location, such as above the table 399. Therefore, any of the subjects wearing the first head-mountable device 200a, second head-mountable device 200b, third head-mountable device 200c, fourth head-mountable device 200d and fifth head-mountable device 200e may view the shared virtual object 710 from different angles, and the shared virtual object 710 may pass from the view of any the subjects.

In an embodiment, a two-dimensional (2D) display may be placed in the shared virtual object 710, and information from one or more specified sources may be provided via the 2D display. Still further, sensors within the first head-mountable device 200a, second head-mountable device 200b, third head-mountable device 200c, fourth head-mountable device 200d and fifth head-mountable device 200e may sense the direction in which the subjects' heads are turned and even the direction in which the subjects' eyes are looking. As a result, a 2D display within the shared virtual object 710 may be particularly oriented in the direction of each subject to maximize the ability of each subject to view information displayed on the 2D display. That is, even though five subjects wearing the head-mountable devices 200a-200e may be located around the table 399 and the shared virtual object 710, a 2D information display within the shared virtual object may appear to each subject to face each subject directly. The barrel shape of the shared virtual object 710 in FIG. 7 may be specifically provided to ensure that a 2d information display within can be oriented in any lateral direction without encroaching on another fixed virtual object.

FIG. 8 illustrates an exemplary space with a shared virtual object fixed at a location within the fields of vision for multiple subjects wearing head-mountable devices, in accordance with an aspect of the present disclosure. In FIG. 8, three different fields of vision 800a, 800b, 800c are generally representative of the viewpoints of the first head-mountable device 200a, the second head-mountable device 200b and the third head-mountable device 200c in FIGS. 3 and 7. The table 399 is shown at various relative locations in the fields of vision 800a, 800b, 800c. In all three fields of vision 800a-800c, a shared virtual object 810 is shown relatively in the same location at the upper right corner.

In the field of vision 800a, the third head-mountable device 200c and fourth head-mountable device 200d are shown. In field of vision 800b, the fourth head-mountable device 200d and the fifth head-mountable device 200e are shown. In field of vision 800c, the first head-mountable device 200a and second head-mountable device 200b are shown. That is, while the table 399 and other of the five subjects 381-385 may appear at variable locations within the fields of vision 800a, 800b, 800c, the shared virtual object 810 is fixed in an extremity of the field of vision.

A 2D information display may be provided via the shared virtual object 810, such as one or more displays from an information source. In this way, no matter which direction subjects wearing head-mountable devices 200a-200c face, the information from the information sources shown in a 2D information display in the shared virtual object 810 will "follow" the subjects.

Although shared virtual object 810 is shown fixed in the same location of a viewpoint for multiple different users, the location of the shared region, the users may also move either the location of the shared virtual object 810 (i.e., when required in their viewpoint), or the location of a shared portion of the 3D space. That is, a shared portion of the 3D space that provides information to different users may be individually located and/or relocated in different locations of the 3D space by the different users when authorized. Accordingly, the shared virtual object 810 or another shared augmented reality object may be placed wherever that user decides is best for them (i.e. it might be in a different spot for every user).

Figure 9:
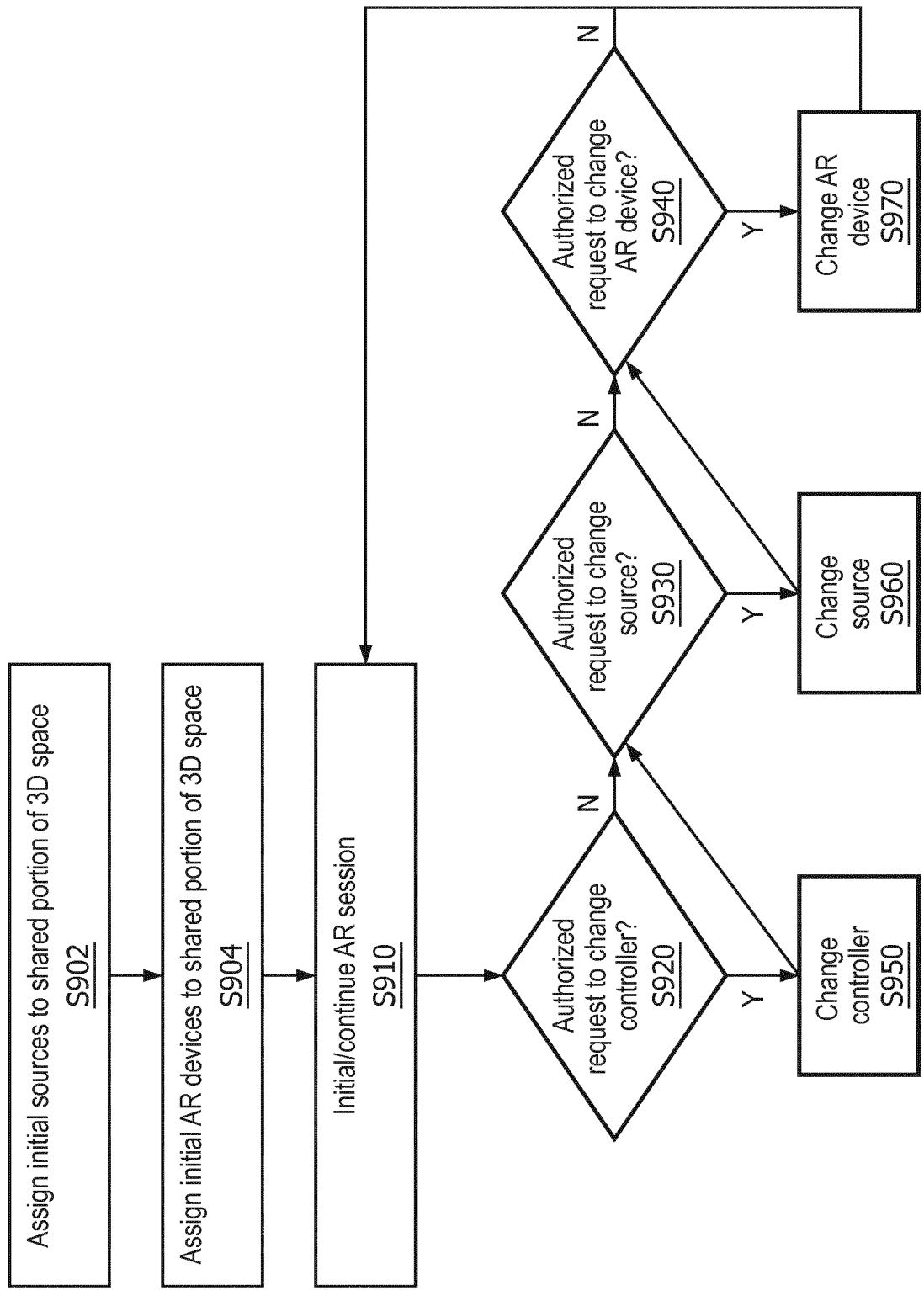
FIG. 9 illustrates a control process for augmented reality for collaborative interventions, in accordance with a representative embodiment.

FIG. 9 illustrates a control process for augmented reality for collaborative interventions, in accordance with a representative embodiment. In FIG. 9, initial sources are assigned to a shared portion of a 3D space at S902. Initial AR devices are assigned to the shared portion of the 3D space at S904. At S910, the AR session is initiated.

A series of checks at S920, S930 and S940 determined whether changes are to be made during the AR session. The check at S920 is whether an authorized request to change the controller has been made. If the controller is to be changed, the controller is changed at S950. Regardless of whether the controller is to be changed, a next determination at S930 is whether an authorized request to change a source has been made. If a source is to be changed, the source is changed at S960. Regardless of whether the source is to be changed, a next determination at S940 is whether an authorized request to change an AR device has been made. If the AR device is to be changed, the AR device is changed at S970. Regardless of whether the AR device is to be changed, the process returns to continue the AR session at S910.

Additionally, while control of a shared region may involve control of a source of data in the shared region, the control may also involve controlling features in the shared region such as a pointer or a trigger. For example, control may involve who is authorized to manipulate (rotate, enlarge, position) a 3D model in the shared region and who gets to place a target on the 3D model? The controls for a 3D model may therefore involve who is authorized to perform different functions in a shared region. In an embodiment, a user may be able to manipulate an object in the shared region in their own view, but the control may involve whether the manipulation is shown to others in their views. In other words, control of a shared region may in some embodiments involve whether a user's input (manipulation within a shared region) will be distributed to others. Several examples illustrating control of a shared portion of a 3D space are shown in and described below with respect to FIGS. 16A-16C.

As described above, in FIG. 9 control of a shared portion of a 3D space can be exercised during an AR session, so that control of sources and destinations (AR devices) can be varied. The control in FIG. 9 can be exercised by a single controller, such as a computer or headset, until the control is passed to another controller in accordance with predetermined authorizations.

Figure 10:
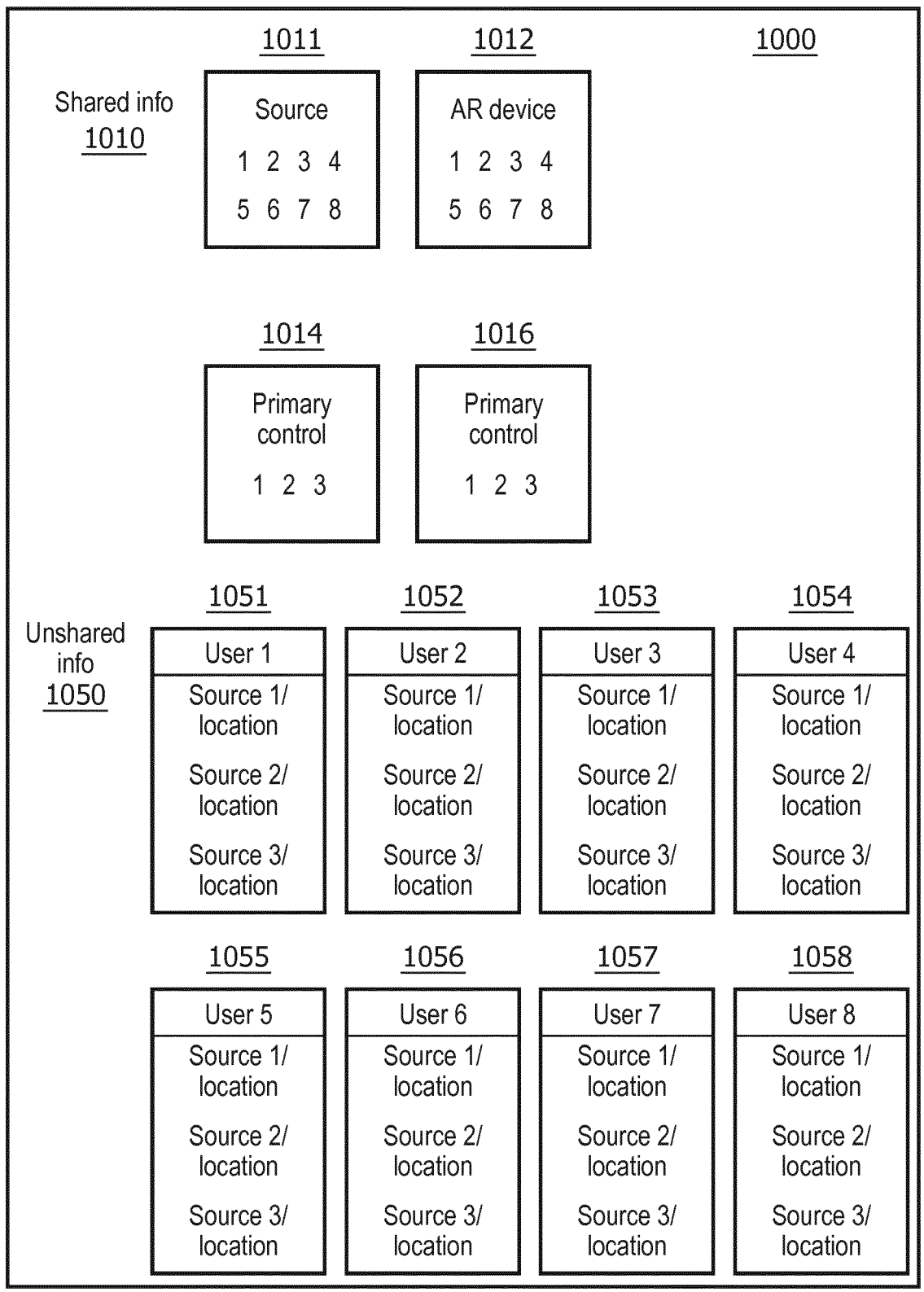
FIG. 10 illustrates a control table for augmented reality for collaborative interventions, in accordance with a representative embodiment.

FIG. 10 illustrates a control table for augmented reality for collaborative interventions, in accordance with a representative embodiment. In FIG. 10, a control table 1000 includes a shared information section 1010 and an unshared information section 1050. The shared information section 1010 includes a source section 1011, a primary control section 1014 for the source section 1011, an AR display section 1012, and a primary control section 1016 for the AR display section 1012. The control table in FIG. 10 may be used to allow selections of eight sources numbered #1, #2, #3, #4, #5, #6, #7 and #8 and eight AR devices numbered #1, #2, #3, #4, #5, #6, #7 and #8 as well as selection of three primary controllers numbered #1, #2 and #3 for each. That is, in FIG. 10, the source section 1011 may be selected independent of the AR display section 1012, such that control of a shared portion may be distributed for different aspects of the control.

In FIG. 10, eight (8) separate AR devices 1051-1058 may each be associated with up to three sources for unshared information. That is, in FIG. 10, different AR devices such as headsets can be associated with unshared information, such as information particular to responsibilities of an individual user. As an example, an X-ray technician may be assigned pre-interventional X-rays as a source, so that the X-rays can be easily referenced during a medical intervention corresponding to an AR session.

Figure 11:
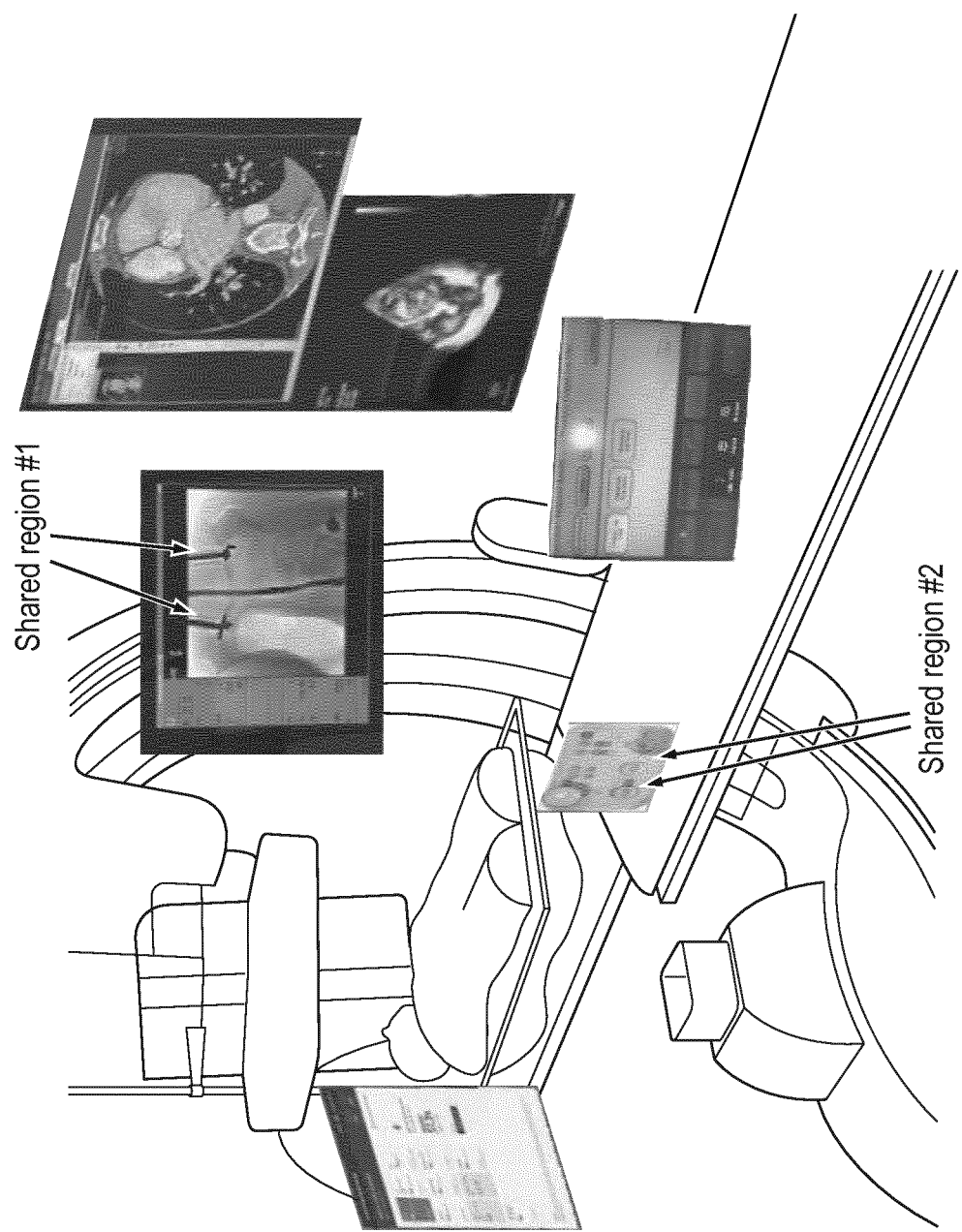
FIG. 11 illustrates a 3D space for augmented reality with collaborative interventions, in accordance with a representative embodiment.

FIG. 11 illustrates a 3D space for augmented reality with collaborative interventions, in accordance with a representative embodiment. In FIG. 11, a view is shown for user where a region of their view has been identified as a shared region. The user is authorized to change content in the shared region, and can drag and drop screens into the region to share with other people provided with the shared region. The user may have multiple shared regions that share the view with different groups of other people. In FIG. 11, two different regions are highlighted as different shared regions, i.e., shared region #1 and shared region #2.

In FIG. 11, different shared regions may be highlighted in different colors, such as a yellow border or shading for a first shared region controlled by a user and a green border or shading for a second shared region controlled by the same user. Other screens that are unshared (i.e., for the user's personal viewing) may be highlighted in a third color or not at all.

A dedicated shared region may be the same fixed location in the room for all users with access to the dedicated shared region, as was the case with shared virtual object 710 in FIG. 7, and as may be useful when, for example, a virtual screen is overlaid onto an existing physical object in the 3D space. Additionally, a screen within a dedicated shared region may be oriented perpendicular to each user in a 3D space, as determined using sensors of the augmented reality devices used by the users. Additionally, a 3D hologram may be shared as an augmented reality object.

As examples, a virtual screen may be overlaid onto a patient in areas not subject to the intervention, or onto a physical display screen in the 3d space. The augmented reality region can be anchored to the 3d space using the standard environment mapping that is known, so that any user of augmented reality using the 3D space can be provided with the same augmented reality object if so authorized. The mapping described already can include object recognition and marker detection to precisely anchor portable/movable objects such as movable physical displays onto which an augmented reality object is overlaid or otherwise placed.

Additionally, a shared augmented reality region can be a mirrored display, so that each user can set a position of their own shared windows to suit their own view. This is similar to the view of the shared virtual object 810 in FIG. 8, except that each user could then move the location of the shared virtual object 810 in their view. In FIG. 8, the shared virtual object 810 can be a window configured to follow each user to be always visible, which may be important for safety purposes such as when patient vitals or live interventional x-ray image are provided in the shared virtual object 810 required for a group of augmented reality users.

Additionally, a shared region can be hidden either on the command of an authorized user, or based on passing a predetermined stage in an augmented reality session, such as when a specific device is turned off and no longer provides a feed for the shared region. The authorized user can turn a shared window on or off using sensors of an augmented reality device (e.g., headset) or using controls such as a foot pedal in the 3D space.

Additionally, adding users to a shared region can be performed using sensor of an augmented reality device used by a user, such as through voice commands, gestures, or even selecting an augmented reality image of a person from a list. A user may also provide commands for a shared region by looking in the direction of a person in the room and using an 'enabling' command.

As noted with respect to the shared virtual object 810, it may be necessary to force a shared view of an augmented reality object to a group of users, such as for safety purposes. For example, it may be important to push a certain display or view to some or all users when a certain event occurs. In an embodiment described below with respect to FIG. 13, triggers may be set to push a shared "alert" region into views of a group of users. Such triggers may be set, for example, when a medical device monitoring a patient determines that vitals drop below a certain threshold, in which case a vital sign dashboard is pushed into the view of a group of users using augmented reality. As another example, a trigger may be set for when radiation usage surpasses a predetermined threshold, in which case a warning indicator is pushed to the view of a group of users using augmented reality.

Figure 12:
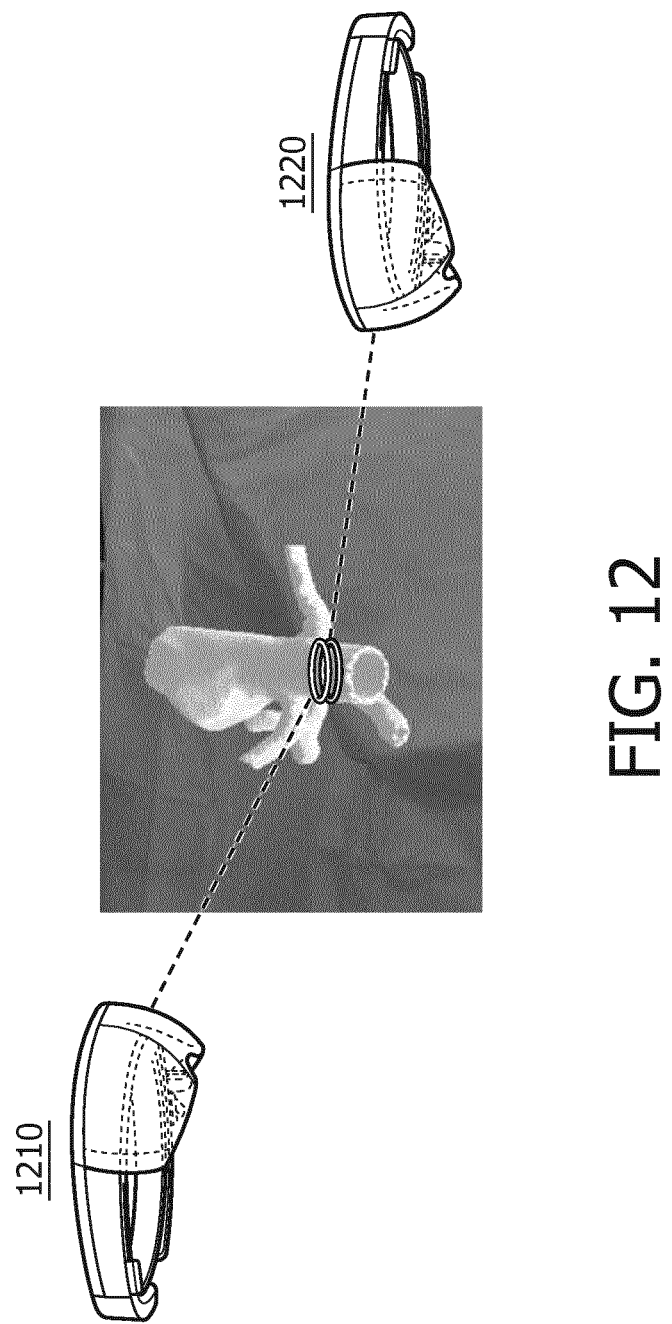
FIG. 12 illustrates collaboration using augmented reality with collaborative interventions, in accordance with a representative embodiment.

FIG. 12 illustrates collaboration using augmented reality with collaborative interventions, in accordance with a representative embodiment. In FIG. 3, two users with two augmented reality devices 1210 and 1220 are shown positioning virtual cursors onto the same target. In this way, two users may interact to show agreement, such as by positioning cursors onto a contact position for a medical instrument. The virtual cursors may be manipulated onto the contact position in a shared portion of a 3D space, so that both augmented reality users can interact even when they are otherwise not physically positioned in locations where it would be possible to physically interact in the same way.

Once users can share a shared portion of a 3D space, such as by given access to a shared object such as an augmented reality screen or hologram, the users may be provided with ways to jointly interact in the context of the shared object. For example, in the medical examples used herein, an echocardiographer and an interventionalist may want to place a target on a 3D hologram together to, for example, such as to agree on an approach to take for a perivalvular leak. The interaction can take place in a few different ways:

- A master-slave configuration where only one user is in control of the interaction at a time.
- A shared configuration where each user can interact, as shown in FIG. 12.
- A virtual overlay on the user's view with 'guiding' interaction by the second user.
- A master enable configuration.

The shared configuration may include an ability to only place a target once both users are indicating the same spot as shown in FIG. 12, such as by controlling the cursor via a gesture, head control etc. The virtual overlay may be particularly useful when a first user is seeing a second user's live view, and the first user can overlay an icon to ask the second user to look around (e.g., left or right, or up or down), or can direct the second user to push a certain button or touch a certain object.

In the master enable configuration, one slave user can be allowed to interact and configure anything in the shared augmented reality window, but the changes can only be put in effect through a master user enable. The master enable configuration may be used to control physical equipment. For example, virtual buttons in the shared region may be provided so that a remote user can interact with the virtual buttons to, for example, position the c-arm or change the image acquisition. The changes can be configured by the remote user but will only take effect once the local user has given authorization via, for example, voice, gesture, foot pedal, button press, etc.

Figure 13:
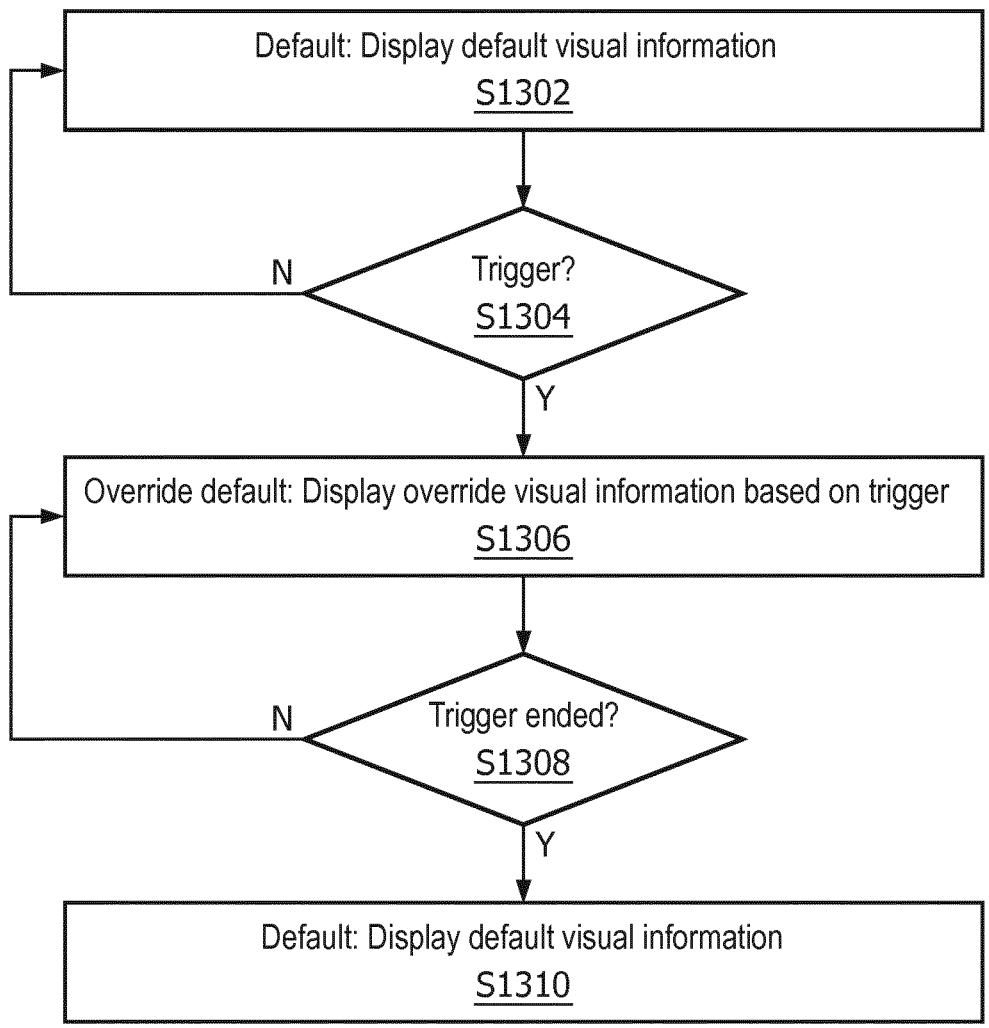
FIG. 13 illustrates another control process for augmented reality for collaborative interventions, in accordance with a representative embodiment.

FIG. 13 illustrates another control process for augmented reality for collaborative interventions, in accordance with a representative embodiment. In FIG. 13, the process starts with a default display of default visual information at S1302. The default visual information may be from a feed designated by a controller of a shared portion of the 3D space, such as a feed from a piece of equipment monitoring a patient or a feed showing fixed images such as X-ray images.

In the process of FIG. 13, repeated checks are made at S1304 for a trigger. If a trigger is detected at S1304 (S1304=Yes), the default is overridden at S1306, and control of the shared window automatically reverts to information corresponding to the trigger. For example, visual information based on the trigger may be placed in the shared portion of the 3D space, and the default visual information is therefore overridden. The trigger may be a trigger based on a medical condition or an environmental condition (e.g., radiation), and the override visual information may be an alarm displaced in the shared portion of the 3D space.

At A1308, repeated checks are made for whether the trigger ends, such as when a medical condition is resolved. When the trigger ends (S1308=Yes), control of the shared portion of the 3D space reverts to displaying default visual information at S1310.

FIG. 14 illustrates timelines for augmented reality for collaborative interventions, in accordance with a representative embodiment. In FIG. 14, three different shared portion controls 1401, 1402 and 1403 are shown. Each shared portion controls shows varying control of respective shared portions #1, #2 and #3 based on segments of an augmented reality session. In other words, control of the shared portions is preplanned according to FIG. 14, so that control passes from one user to the next based on the segment of the timeline the augmented reality session is in. Of course, control may be overridden using triggers as in FIG. 13, or when the default user given control designates another user to have control of the shared portion of the 3D space for their segment.

Figure 15C:
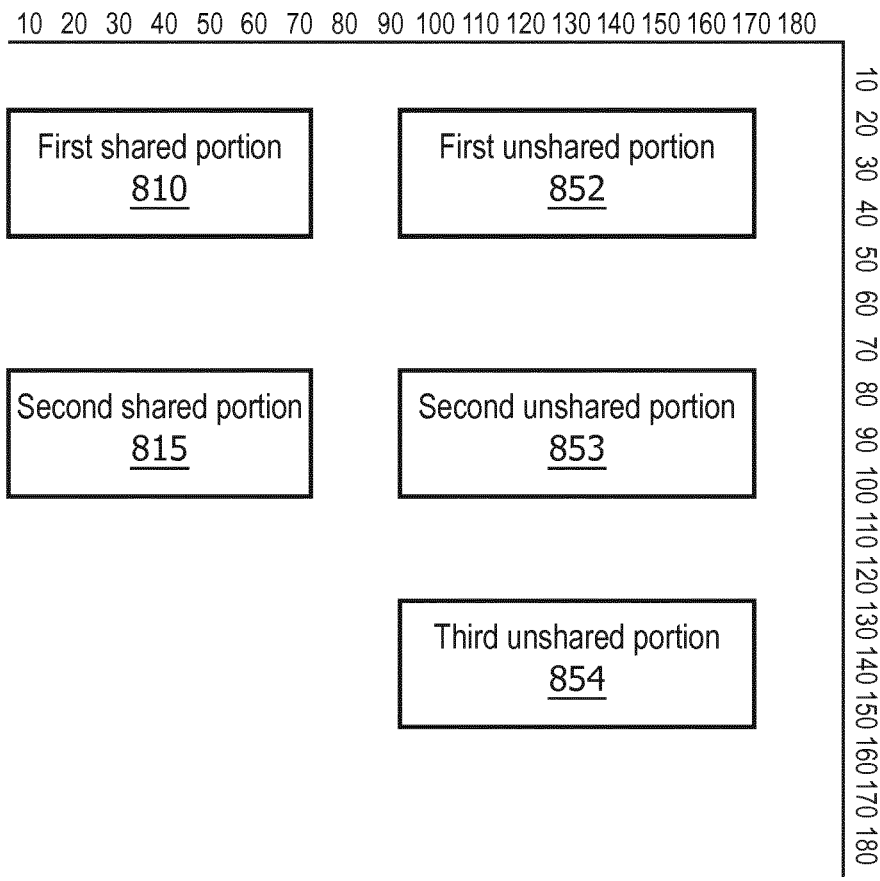

FIGS. 15A-15C illustrate fields of view for three separate augmented reality devices for augmented reality for collaborative interventions, in accordance with a representative embodiment. In FIGS. 15A-15C, three different views are shown for different users using augmented reality. For example, in FIG. 15A, a first shared virtual object 810 and a second shared virtual object 815 are shown on the left side of the augmented reality view. In FIG. 15B, the first shared virtual object 810 and the second shared virtual object 815 are shown at the upper part of the augmented reality view. In FIG. 15C, the first shared virtual object 810 and the second shared virtual object 815 are shown on the left side of the augmented reality view, but three unshared portions 852, 853 and 854 are shown on the right side of the augmented reality view. The example of FIG. 15C might be a remote user assigned to monitor different aspects of a medical intervention remotely, such that the remote user will not be overloaded by processing 5 different sources of information simultaneously.

Figure 16A:
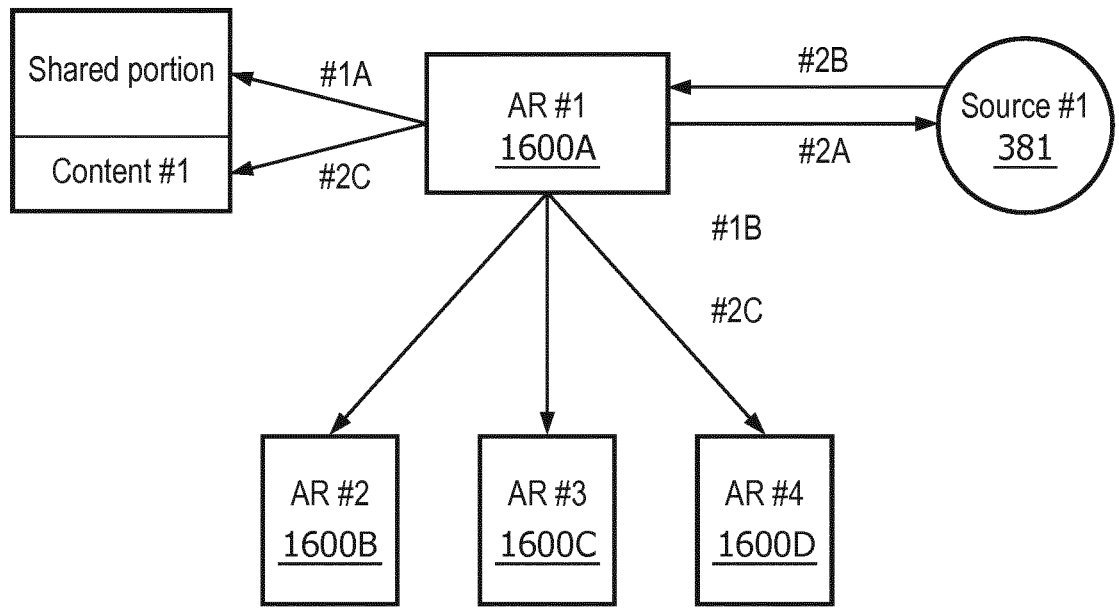
FIG. 16A illustrates a process flow for augmented reality for collaborative interventions, in accordance with representative embodiments.

FIG. 16A illustrates a process flow for augmented reality for collaborative interventions, in accordance with representative embodiments. In FIG. 16A, augmented reality display device #1 1600A initially creates the shared portion at process step 1A and informs augmented reality display devices #2 1600B, #3 1600C and #4 1600D at process step 1B. At process step 2A, augmented reality display device #1 1600A requests source #1 381 to provide content for the shared portion, and at process step 2B source #1 381 provides content #1 to augmented reality display device #1 1600A for the shared portion. At process step 2C, augmented reality display device #1 1600A populates the shared portion with the content #1 and relays content #1 to augmented reality display devices #2 1600B, #3 1600C and #4 1600D so that they will each do the same.

Accordingly, in the embodiment of FIG. 16A, the shared portion, data defining the shared portion, and content #1 populating the shared portion are coordinated and controlled by augmented reality display device #1. In order to interact in the shared portion, any of augmented reality display devices #2 1600B, #3 1600C and #4 1600D can request augmented reality display device #1 to display additional data. As an example, the shared portion may be a data layer superimposed on content #1 and any other content from other sources. Any of augmented reality display devices #2 1600B, #3 1600C and #4 1600D can provide data indicating a cursor to augmented reality display device #1 1600A such that augmented reality display device #1 1600A controls the data layer defining the shared portion. Augmented reality display device #1 1600A may add the cursor to the data layer so that the shared portion is updated for all augmented reality display devices #1 1600A, #2 1600B, #3 1600C and #4 1600D in a next refresh. The data layer defining the shared portion may be refreshed and updated frequently, such as between 2 and 100 times per second, so that even if each of augmented reality display devices #2 1600B, #3 1600C and #4 1600D all provide their own cursors for simultaneous display in the shared portion, the cursors will appear together to all other devices with access to the shared space in real-time or near real-time. As noted, the data layer defining the shared portion in this embodiment is controlled by augmented reality display device #1 1600A, so all requests to add data are coordinated and controlled by augmented reality display device #1 1600A.

Figure 16B:
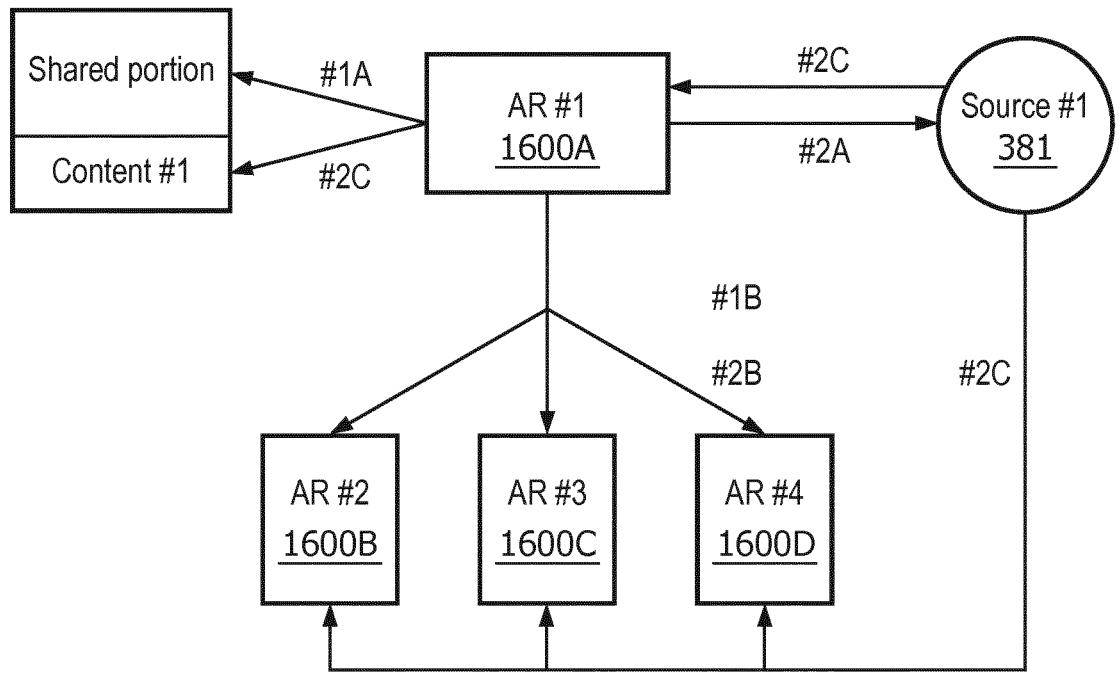
FIG. 16B illustrates another process flow for augmented reality for collaborative interventions, in accordance with representative embodiments.

FIG. 16B illustrates another process flow for augmented reality for collaborative interventions, in accordance with representative embodiments. In FIG. 16B, augmented reality display device #1 1600A again initially creates the shared portion at process step 1A and informs augmented reality display devices #2 1600B, #3 1600C and #4 1600D at process step 1B. At process step 2A, augmented reality display device #1 1600A requests source #1 381 to provide content for the shared portion directly to each of augmented reality display devices #2 1600B, #3 1600C and #4 1600D, and at process step 2B source #1 381 so informs augmented reality display devices #2 1600B, #3 1600C and #4 1600D. At process step 2C, source #1 381 provides the content to all of the augmented reality display devices #1 1600A, #2 1600B, #3 1600C and #4 1600D, such as by individually addressing content #1 directly of the different devices.

Accordingly, in the embodiment of FIG. 16B, the shared portion and data defining the shared portion are coordinated and controlled by augmented reality display device #1, but the content #1 is separately provided by source #1 381. Nevertheless, for the purposes of interacting in the shared portion, the embodiment of FIG. 16B will operate the same as the embodiment of FIG. 16A. That is, any of augmented reality display devices #2 1600B, #3 1600C and #4 1600D can request augmented reality display device #1 to display additional data, such as when the shared portion is a data layer superimposed on content #1 and any other content from other sources. Any of augmented reality display devices #2 1600B, #3 1600C and #4 1600D can provide data indicating a cursor to augmented reality display device #1 1600A such that augmented reality display device #1 1600A controls the data layer defining the shared portion. Augmented reality display device #1 1600A may add the cursor to the data layer so that the shared portion is updated for all augmented reality display devices #1 1600A, #2 1600B, #3 1600C and #4 1600D in a next refresh. As noted, the data layer defining the shared portion is controlled by augmented reality display device #1 1600A, so all requests to add data are coordinated and controlled by augmented reality display device #1 1600A.

Figure 16C:
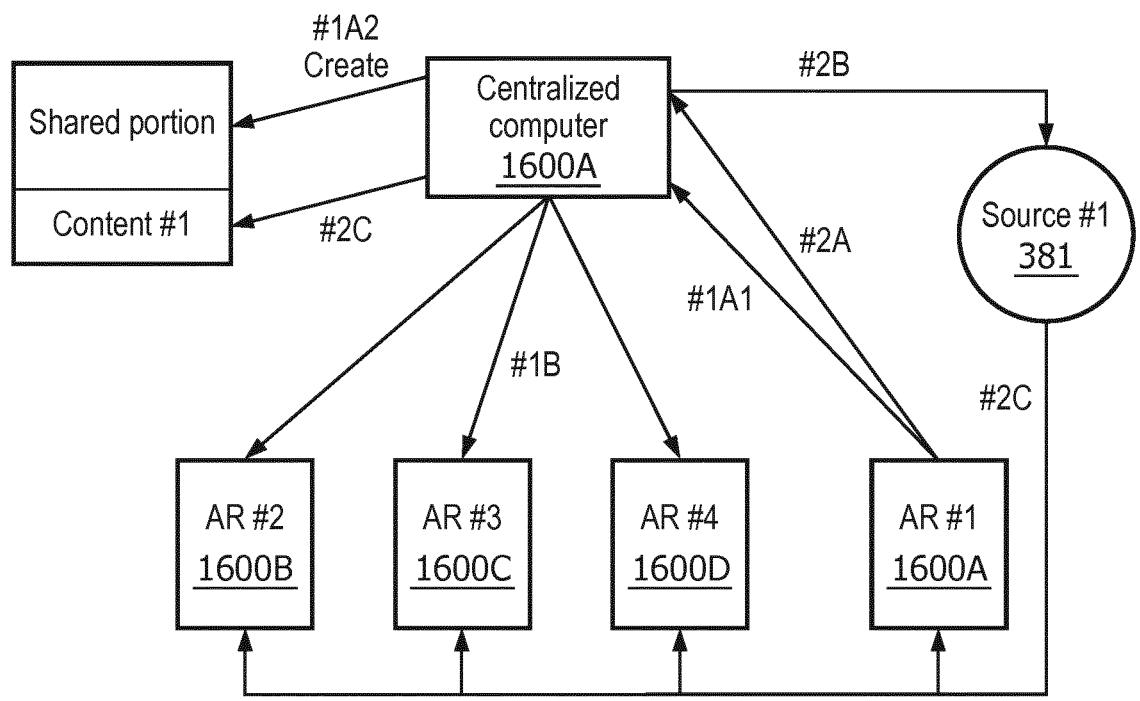
FIG. 16C illustrates another process flow for augmented reality for collaborative interventions, in accordance with representative embodiments.

FIG. 16C illustrates another process flow for augmented reality for collaborative interventions, in accordance with representative embodiments. In FIG. 16C, centralized computer 390 creates the shared portion at process step 1A1 based on a request from augmented reality display device #1 1600A. At process step 1A2, centralized computer 390 creates the shared space and at process 1B the centralized computer 390 informs all other augmented reality display devices #2 1600B, #3 1600C and #4 1600D. At process step 2A, augmented reality display device #1 1600A requests source #1 381 to provide content for the shared portion, and process step 2B, centralized computer 390 contacts source #1. At process step #2C, source #1 381 provides the content #1 directly to all four augmented reality display devices #1, 1600A, #2 1600B, #3 1600C and #4 1600D. Of course, source #1 381 may alternatively provide content #1 directly to centralized computer 390, and centralized computer 390 may relay content #1 to all augmented reality display devices #1 1600A, #2 1600B, #3 1600C and #4 1600D.

Accordingly, in the embodiment of FIG. 16C, the shared portion, data defining the shared portion, and possibly even the content #1 from source #1 381 can all be coordinated and controlled by centralized computer 390, such as at the request of augmented reality display device #1 1600A. For the purposes of interacting in the shared portion, the embodiment of FIG. 16C will operate by requiring all requests to be coordinated and controlled by the centralized computer 390. That is, any of augmented reality display devices #1 1600A, #2 1600B, #3 1600C and #4 1600D can request centralized computer 390 to display additional data, such as when the shared portion is a data layer superimposed on content #1 and any other content from other sources. Any of augmented reality display devices #1 1600A, #2 1600B, #3 1600C and #4 1600D can provide data indicating a cursor to centralized computer 390, such that centralized computer 390 controls the data layer defining the shared portion. Centralized computer 390 may add the cursor to the data layer so that the shared portion is updated for all augmented reality display devices #1 1600A, #2 1600B, #3 1600C and #4 1600D in a next refresh. As noted, the data layer defining the shared portion is controlled by the centralized computer 390, so all requests to add data are coordinated and controlled by centralized computer 390.

Although the embodiments of FIGS. 16A-16C are described in the context of 2D screens with content #1, the shared portion may also be a 3D space with 3D content. Thus, cursors or even 3D objects may be permissively superimposed on 3D content in a shared portion consistent with any of these embodiments, such as by the coordination and control of a single controller.

Additionally, while the examples of interaction described above mainly use cursors for consistency, interaction may also include, for example, pushing virtual buttons, or moving characters individually on a board such as to correct one another's spelling. Thus, interaction would be understood as including many different forms of virtual interaction made possible in a shared portion and analogous to physical interaction in a physical space.

Accordingly, augmented reality for collaborative interventions enables multiple different kinds of control of a shared portion of a 3D space. The controller in control of the shared portion can change sources of information provided via the shared portion, can change augmented reality devices authorized to (or even required to) access the shared portion, and can change control of the shared portion by passing control to another controller.

Though a variety of embodiments are shown herein using augmented reality headsets, augmented reality controllers for a shared portion of a 3D space can also be provided to a centralize computer 390 in the 3D space, or even remote computers.

Additionally, while aspects of the control are shown to be preplanned for augmented reality sessions in different embodiments herein, control may be dynamically initiated or changed during an augmented reality session. For example, an authorized user may enter an operating room (i.e., a 3D space) with an augmented reality headset, and activate a shared portion of the 3D space via sensors of the augmented reality headset. The authorized user may, for example, announce that information from designated sources should be provided to a predesignated augmented reality portion of the operating room. Alternatively, the authorized user may use gestures to initiate a shared portion, and designated sources and recipients.

Although augmented reality for collaborative interventions has been described with reference to several exemplary embodiments, it is understood that the words that have been used are words of description and illustration, rather than words of limitation. Changes may be made within the purview of the appended claims, as presently stated and as amended, without departing from the scope and spirit of augmented reality for collaborative interventions in its aspects. Although augmented reality for collaborative interventions has been described with reference to particular means, materials and embodiments, augmented reality for collaborative interventions is not intended to be limited to the particulars disclosed; rather augmented reality for collaborative interventions extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

According to an aspect of the present disclosure, a controller for augmenting reality includes a memory that stores instructions, and a processor that executes the instructions. The controller receives, from at least one device that provides output via a display, an information feed including first visual information from the at least one device. When executed by the processor, the instructions cause the controller to execute a process that includes controlling generation of first visual information in a first shared portion of a 3D space by a first augmented reality device as augmented reality. The process also includes controlling generation of the first visual information in the first shared portion of the 3D space by a second augmented reality device as augmented reality.

According to another aspect of the present disclosure, the at least one device is monitoring equipment that monitors a subject in the 3D space.

According to yet another aspect of the present disclosure, the at least one device is medical equipment that monitors a medical condition of a subject in the 3D space.

According to still another aspect of the present disclosure, the controller is implemented in the first augmented reality device and passes control of the first shared portion to the second augmented reality device during an augmented reality session According to another aspect of the present disclosure, the controller controls generation of second visual information in a first unshared portion of the 3D space by the first augmented reality device as augmented reality.

According to yet another aspect of the present disclosure, the controller passes control of the first shared portion to another controller based on instructions received dynamically during an augmented reality session.

According to still another aspect of the present disclosure, the controller passes control of the first shared portion to another controller based on passage of a predetermined stage of an augmented reality session, in accordance with predetermined instructions set before the augmented reality session.

According to another aspect of the present disclosure, the controller is implemented in a centralized computer that is linked to the first augmented reality device and the second augmented reality device.

According to yet another aspect of the present disclosure, a location of the first shared portion is independently variable for each of the first augmented reality device and the second augmented reality device.

According to still another aspect of the present disclosure, a location of the first shared portion is fixed for each of the first augmented reality device and the second augmented reality device.

According to another aspect of the present disclosure, the first visual information is automatically updated based on a trigger so that each of the first augmented reality device and the second augmented reality device are controlled by the controller to receive updated information in the first shared portion based on the trigger.

According to an aspect of the present disclosure, a method of operating a controller for augmenting reality in a 3D space includes storing instructions in a memory of the controller. The method includes receiving, at the controller and from a first device that provides output via a display, a first information feed including first visual information. The method also includes executing the instructions by a processor of the controller to perform a process. The process includes controlling generation of the first visual information in a first shared portion of a 3D space by a first augmented reality device as augmented reality. The process also includes controlling generation of the first visual information in the first shared portion of the 3D space by a second augmented reality device as augmented reality.

According to another aspect of the present disclosure, the controlling generation of the first visual information is performed by dynamically receiving a request to authorize displaying of the first visual information in the first shared portion of the 3D space, and selectively authorizing the request to display the first visual information.

According to yet another aspect of the present disclosure, the method includes receiving a request to change the first information feed including first visual information from the first device to a second information feed including second visual information from a second device. The method also includes controlling generation of the second visual information in the first shared portion by the first augmented reality device as augmented reality. The method further includes controlling generation of the second visual information in the first shared portion of the 3D space by the second augmented reality device as augmented reality.

According to still another aspect of the present disclosure, the passing control of the first shared portion to another controller based on an instruction dynamically received from a user during an augmented reality session.

According to another aspect of the present disclosure, the method also includes passing control of the first shared portion to another controller based on passing of a predetermined stage of an augmented reality session.

According to yet another aspect of the present disclosure, the first augmented reality device includes a head-mountable augmented reality device.

According to still another aspect of the present disclosure, the 3D space is a pre-defined physical environment on which virtual objects are superimposed by the first augmented reality device and the second augmented reality device.

According to another aspect of the present disclosure, the method also includes selectively enabling a first user to place content in the first shared portion of the 3D space.

According to yet another aspect of the present disclosure, the method also includes selecting enabling a second user to alter content placed in the first shared portion by the first user.

According to another aspect of the present disclosure, the first augmented reality device is configured to present a live feed from the second augmented reality device, and a user of the first augmented reality device is enabled to interact with a virtual object in the live feed from the second augmented reality device so that interaction between the first user and the virtual object is presented to a second user of the second augmented reality device.

According to an aspect of the present disclosure, a system for augmenting reality includes a first head-mountable device and a second head-mountable device. The first head-mountable device includes a first processor that generates a display of first visual information in a first shared portion as augmented reality. The second head-mountable device includes a second processor that generates a display of the first visual information in the first shared portion as augmented reality, and that generates a display of second visual information in a first unshared portion as augmented reality. The system controls information display of the first visual information in the first shared portion and the second visual information in the first unshared portion. The system varies control of the first shared portion.

According to another aspect of the present disclosure, the system includes a third head-mountable device that includes a second unshared portion and displays third visual information different than the second visual information in the second unshared portion.

According to still another aspect of the present disclosure, the system is configured to supplement a live image stream using augmented reality and information generated by a computer.

According to yet another aspect of the present disclosure, the system is enclosed in a space in which people wear the head-mountable devices.

According to another aspect of the present disclosure, the first head-mountable device and second head-mountable device are continuously linked by a communication connection.

According to still another aspect of the present disclosure, the system includes a centralized computer that is linked wirelessly to the first head-mountable device and the second head-mountable device, that includes a memory that stores instructions and a processor that executes the instructions, and that controls the information display of the first visual information in the first shared portion.

According to yet another aspect of the present disclosure, the first head-mountable device is configured to control the information display of the first visual information in the first shared portion.

According to another aspect of the present disclosure, control of the information display of the first visual information in the first shared portion is variably change between the first head-mountable device and the second head-mountable device.

According to still another aspect of the present disclosure, a location of the first shared portion is independently variable for each of the first head-mountable device and the second head-mountable device.

According to yet another aspect of the present disclosure, a location of the first shared portion is fixed for each of the first head-mountable device and the second head-mountable device.

According to another aspect of the present disclosure, the system includes a third head-mountable device that includes a third processor that generates a display of third visual information in a second shared portion as augmented reality. The first processor generates a display of the third visual information in the second shared portion as augmented reality.

According to still another aspect of the present disclosure, the first shared portion is fixed in a 3D space that includes the system as the first head-mountable device and second head-mountable device move within the 3D space.

According to yet another aspect of the present disclosure, the first shared portion is fixed in a field of view of the first head-mountable device.

According to another aspect of the present disclosure, control of the first shared portion varies in stages under the control of a user.

According to still another aspect of the present disclosure, the first visual information is automatically updated based on a trigger so that each of the first head-mountable device and the second head-mountable device are provided with updated information based on the trigger.

According to an aspect of the present disclosure, a system for augmenting reality in a 3D space includes a first display and a second display. The first display is head-mountable and includes a first display system configured to present virtual objects in the 3D space, at least one first sensor configured to sense a pose of a first user in the 3D space, and a first processor configured to control presentation of first visual information by the first display system in a first shared portion of the 3D space as augmented reality. The second display is physically separate from the first head-mountable device and includes a second display system configured to present virtual objects in the 3D space, and a second processor that is configured to control presentation of the first visual information by the second display system in the first shared portion of the 3D space and configured to control presentation of second visual information by the second display system in a first unshared portion of the 3D space as augmented reality. Control of the first shared portion of the 3D space dynamically varies while the first user is in the 3D space.

According to another aspect of the present disclosure, the second display is head-mountable and further includes at least one second sensor configured to sense a pose of a second user in the 3D space.

According to still another aspect of the present disclosure, the 3D space is based on a pre-defined physical environment on which the virtual objects are superimposed by the first display system and second display system.

According to yet another aspect of the present disclosure, the 3D space varies between the first display and a second display based on the first unshared portion.

According to another aspect of the present disclosure, the first user and the second user are each enabled to place content in the first shared portion of the 3D space.

According to still another aspect of the present disclosure, content placed in the first shared portion of the 3D space by the first user can be altered by the second user. Content placed in the first shared portion of the 3D space by the second user can be altered by the first user.

According to yet another aspect of the present disclosure, the first display system is configured to present a live feed from the second display, and the first user is enabled to interact with a virtual object in the live feed from the second display so that interaction between the first user and the virtual object is presented to the second user.

According to another aspect of the present disclosure, the first user is enabled to interact with a virtual object in the first shared portion. The second user is prevented from interacting with the virtual object in the first shared portion.

According to still another aspect of the present disclosure, the first user is selectively enabled to interact with a virtual object in the first shared portion. The second user selectively enables the first user to interact with the virtual object in the first shared portion.

One or more embodiments of the disclosure may be referred to herein, individually and/or collectively, by the term "invention" merely for convenience and without intending to voluntarily limit the scope of this application to any specific invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment to streamline the disclosure. This disclosure is not to be interpreted as reflecting an intention that the claimed embodiments require more features than are expressly recited in each claim. Rather, as the following claims reflect, inventive subject matter may be directed to less than all features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A controller for augmenting reality, comprising:
a memory that stores instructions; and
a processing circuitry configured to execute the instructions,
wherein, the controller receives, from at least one imaging device that provides output via a display, an information feed comprising first visual information of a patient captured by the imaging device, and
wherein, when executed by the processing circuitry, the instructions cause the controller to:
control generation of first visual information in a first shared portion of a three-dimensional (3D) space by a first augmented reality device as augmented reality by the first augmented reality device, and
control generation of the first visual information in the first shared portion of the 3D space by a second augmented reality device as augmented reality by the second augmented reality device.

2. The controller of claim 1,
wherein the controller is implemented in the first augmented reality device and passes control of the first shared portion to the second augmented reality device during an augmented reality session.

3. The controller of claim 1,
wherein the controller controls generation of second visual information in a first unshared portion of the 3D space by the first augmented reality device as augmented reality.

4. The controller of claim 1,
wherein the controller passes control of the first shared portion to another controller based on instructions received dynamically during an augmented reality session.

5. The controller of claim 1,
wherein the controller passes control of the first shared portion to another controller based on passage of a predetermined stage of an augmented reality session, in accordance with predetermined instructions set before the augmented reality session.

6. The controller of claim 1,
wherein the controller is implemented in a centralized computer that is linked to the first augmented reality device and the second augmented reality device.

7. The controller of claim 1,
wherein a location of the first shared portion is independently variable for each of the first augmented reality device and the second augmented reality device.

8. The controller of claim 1,
wherein a location of the first shared portion is fixed for each of the first augmented reality device and the second augmented reality device.

9. The controller of claim 1, wherein the patient is located in the 3D space.

10. The controller of claim 1, wherein the imaging device is configured to provide, in the first information feed, visual information corresponding to the anatomy of the patient.

11. A method of operating a controller for augmenting reality in a three-dimensional (3D) space, comprising:
storing instructions in a memory of the controller;
receiving, at the controller and from a first imaging device that provides output via a display, a first information feed comprising first visual information of a patient captured by the imaging device; and
executing the instructions by a processor of the controller to perform a process comprising:
controlling generation of the first visual information in a first shared portion of the 3D space by a first augmented reality device as augmented reality by the first augmented reality device, and
controlling generation of the first visual information in the first shared portion of the 3D space by a second augmented reality device as augmented reality by the second augmented reality device.

12. The method of claim 11, further comprising:
receiving a request to change the first information feed comprising first visual information from the first device to a second information feed comprising second visual information from a second device, and
controlling generation of the second visual information in the first shared portion by the first augmented reality device as augmented reality, and controlling generation of the second visual information in the first shared portion of the 3D space by the second augmented reality device as augmented reality.

13. The method of claim 11, further comprising:
passing control of the first shared portion to another controller based on an instruction dynamically received from a user during an augmented reality session.

14. The method of claim 11, further comprising:
passing control of the first shared portion to another controller based on passing of a predetermined stage of an augmented reality session.

15. The method of claim 11,
wherein the 3D space comprises a pre-defined physical environment on which virtual objects are superimposed by the first augmented reality device and the second augmented reality device.

16. The method of claim 11, further comprising:
selectively enabling a first user to place content in the first shared portion of the 3D space.

17. The method of claim 16, further comprising:
selecting enabling a second user to alter content placed in the first shared portion by the first user.

18. The method of claim 11,
wherein the first augmented reality device is configured to present a live feed from the second augmented reality device, and a user of the first augmented reality device is enabled to interact with a virtual object in the live feed from the second augmented reality device so that interaction between a first user and the virtual object is presented to a second user of the second augmented reality device.

19. The method of claim 11, wherein the patient is located in the 3D space.

20. The method of claim 11, wherein the imaging device is configured to provide, in the first information feed, visual information corresponding to the anatomy of the patient.

* * * * *